(12) United States Patent
Eldershaw et al.

(10) Patent No.: US 9,797,857 B2
(45) Date of Patent: Oct. 24, 2017

(54) SYSTEMS FOR ELECTROCHEMICAL SORTING OF METALS AND ALLOYS

(71) Applicant: Palo Alto Research Center Incorporated, Palo Alto, CA (US)

(72) Inventors: Craig Eldershaw, Belmont, CA (US); Saroj Sahu, Fremont, CA (US); Sean Garner, San Francisco, CA (US); Ranjeet Rao, Redwood City, CA (US); Ashutosh Kole, San Francisco, CA (US); Vedasri Vedharathinam, San Jose, CA (US); Divyaraj Desai, San Jose, CA (US); Jessica Louis Baker Rivest, Palo Alto, CA (US); Richard Steele, Newark, CA (US); Martin J. Sheridan, Redwood City, CA (US)

(73) Assignee: PALO ALTO RESEARCH CENTER INCORPORATED, Palo Alto, CA (US)

( * ) Notice: Subject to any disclaimer, the term of this patent is extended or adjusted under 35 U.S.C. 154(b) by 243 days.

(21) Appl. No.: 14/626,332

(22) Filed: Feb. 19, 2015

(65) Prior Publication Data

US 2016/0245773 A1 Aug. 25, 2016

(51) Int. Cl.
*G01N 27/413* (2006.01)
*G01N 27/31* (2006.01)
*G01N 27/38* (2006.01)
*G01N 33/20* (2006.01)
*G01N 27/416* (2006.01)

(52) U.S. Cl.
CPC .............. *G01N 27/31* (2013.01); *G01N 27/38* (2013.01); *G01N 27/413* (2013.01); *G01N 27/416* (2013.01); *G01N 33/20* (2013.01)

(58) Field of Classification Search
CPC .... G01N 27/26–27/302; G01N 27/308–27/32; G01N 27/333–27/401; G01N 27/403–27/4045; G01N 27/411–27/413
USPC ................ 204/194, 400, 404–407, 412, 414, 204/415–420, 430–435; 205/775.5–777, 205/790, 790.5–791.5, 794.5
See application file for complete search history.

(56) References Cited

U.S. PATENT DOCUMENTS

| 4,190,501 | A |   | 2/1980  | Riggs, Jr.              |
|-----------|---|---|---------|-------------------------|
| 4,294,667 | A | * | 10/1981 | Yamamoto ....... G01N 22/04 204/404 |
| 5,080,766 | A |   | 1/1992  | Moment et al.           |
| 5,218,303 | A |   | 6/1993  | Medvinsky               |
| 5,545,869 | A |   | 8/1996  | Noding                  |

(Continued)

FOREIGN PATENT DOCUMENTS

| EP | 2063263 A2 | 5/2009 |
| FR | 1142731 A  | 9/1957 |

(Continued)

OTHER PUBLICATIONS

EP Search Report 16154251.9-1554 /3050591 dated Jul. 27, 2016.

(Continued)

*Primary Examiner* — Bach Dinh
(74) *Attorney, Agent, or Firm* — Fay Sharpe LLP

(57) ABSTRACT

Disclosed is an electrochemical probe system and an electrical excitation method, configured in a handheld sorting system, and used to identify the composition of metals and alloys.

18 Claims, 21 Drawing Sheets

(56) References Cited

U.S. PATENT DOCUMENTS

| | | | |
|---|---|---|---|
| 5,568,990 A | 10/1996 | McAuley | |
| 5,792,337 A * | 8/1998 | Padovani | G01N 17/02 205/775.5 |
| 6,398,931 B1 | 6/2002 | Burchette et al. | |
| 7,695,601 B2 | 4/2010 | Jiang et al. | |
| 9,316,613 B2 | 4/2016 | Unwin et al. | |
| 2009/0014422 A1* | 1/2009 | Miklos | B23K 5/213 219/75 |
| 2009/0166198 A1 | 7/2009 | Du et al. | |
| 2012/0285827 A1* | 11/2012 | Dunn | G01N 27/416 204/406 |
| 2013/0220807 A1 | 8/2013 | Radomyshelsky et al. | |
| 2014/0096796 A1* | 4/2014 | Frum | A47L 11/1625 134/6 |

FOREIGN PATENT DOCUMENTS

| | | |
|---|---|---|
| GB | 1334597 A | 10/1973 |
| WO | WO 2008/087687 A2 | 7/2008 |

OTHER PUBLICATIONS

EP Search Report 16154254.3-1554 dated Jul. 7, 2016.
A Abal Associacao Brasileira do Aluminio, retrieved from the Internet Dec. 16, 2014, http://www.abal.org.br/, 5 pgs.
Bruker Alloy Tester, Scrap Metal Identification & Sorting with Bruker XRF Scrap Guns, retrieved from the Internet Dec. 16, 2014, http://alloytestercom/scrap-metal-identification, 2 pgs.
Ashahi Kasei E-Materials Corporation, retrieved from the Internet Dec. 16, 2014, http://www.asahi-kasei.co.jp/hipore/en/index.html, 2 pgs.
Buckler, The ec-pen in quality control: Determining the corrosion resistance of stainless steel on-site, International Symposium (NDT-CE 2003), 5 pgs.
Huang, A Fast Two-Dimensional Median Filtering Algorithm, IEEE Transactions on Acoustics, Speech, and Signal Processing, vol. ASSP-27, No. 1, Feb. 1979, pp. 13-18.
Guthrie, Overview of X-ray Fluorescence, Archaeometry Laboratory, Univ. of Missouri Research Reactor, revised Aug. 2012, 9 pgs.
Celgard, Monolayer Polyethylene (PE), retrieved from the Internet Dec. 16, 2014, http://www.celgard.com/monolayer-pe.aspx, 1 pg.
Oxford Instruments, Optical Emission Spectroscopy (OES) for Metal Analysis, retrieved from the Internet Dec. 16, 2014, http://www.oxford-instruments.com/products/spectrometers/optical-emission-spectroscopy, 2 pgs.
Steel Recycling Instistute, Steel Recycling Information, News & Resources, retrieved from the Internet Dec. 16, 2014, http://www.recycle-steel.org, 2 pgs.
U.S. Environmental Protection Agency, Wastes-Resource Conservation—WARM, Wast Reduction Model (WARM), retrieved from the Internet Dec. 16, 2014, 2 pgs.
Freemantle, An Introduction to Ionic Liquids, 2010, published by the Royal Society of Chemistry, Introduction, Chapter 1, 10 pgs.
ARPA-E, Financial Assistance Funding Opportunity Announcement, U.S. Department of Energy, Modern Electro/Thermochemical Advances in Light-Metal Ssytems (Metals), Mar. 20, 2013, 84 pgs.
Median Filtr, Wikipedia, retrieved from the Internet Dec. 16, 2014, http://en.wikipedia.org/wiki/median_filtr, 1 pg.
PARSE: Developing the Future of U.S. Recycling, PARC Blog, Mar. 13-14, 2014, http://blogs.parc.com/blog/2014/02/parse-developing-the-future-of-u-s-recycling/, 2 pgs.
Scrap Specifications Circular 2013, Guidelines for Metals Transactions, Institute of Scrap Recycling Industries, Jul. 24, 2013, 6 pgs.
ASM Specialty Handbook, Aluminum and Aluminum Alloys, Edited by J.R. Davis, Dec. 1993.

* cited by examiner

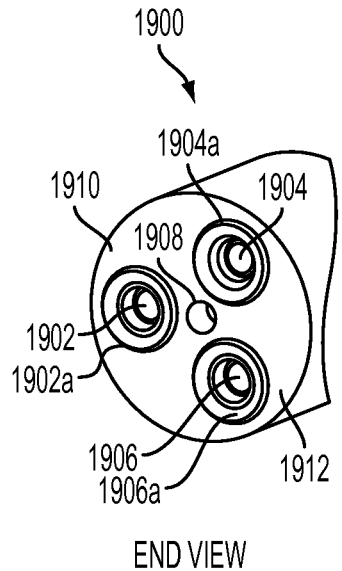
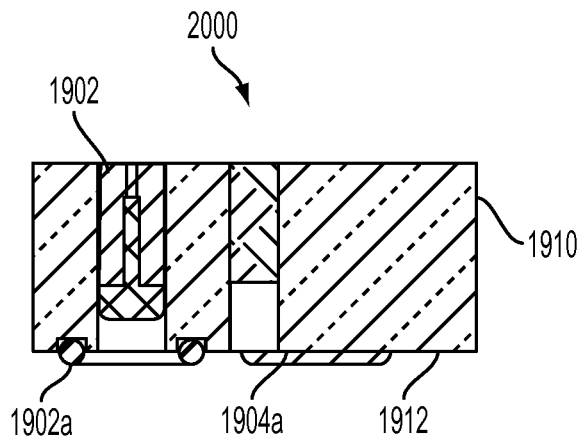
FIG. 19  FIG. 20
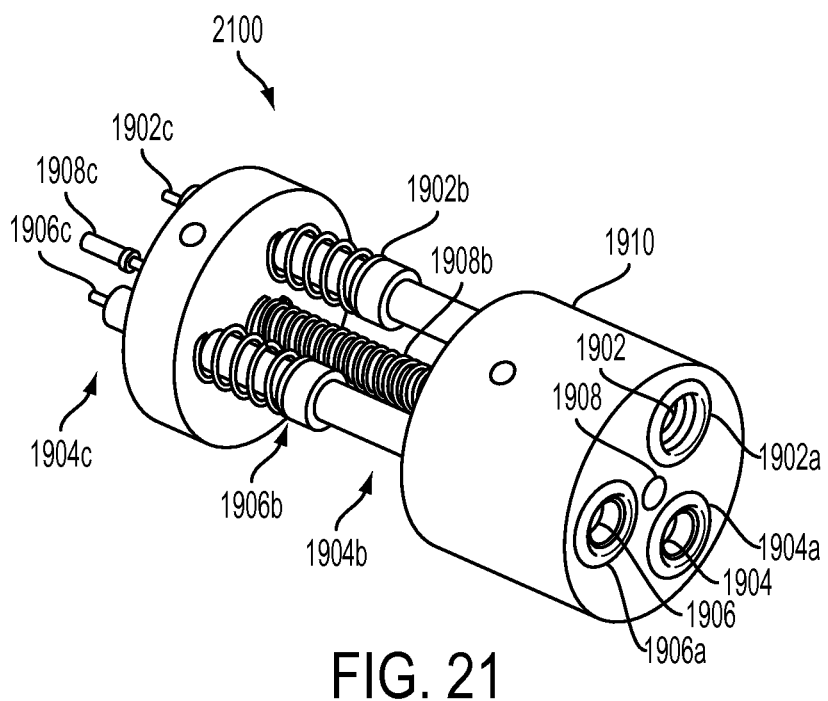
FIG. 21

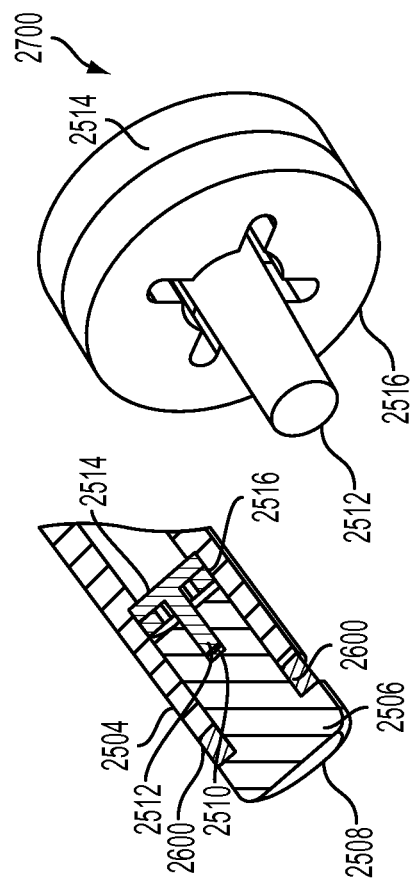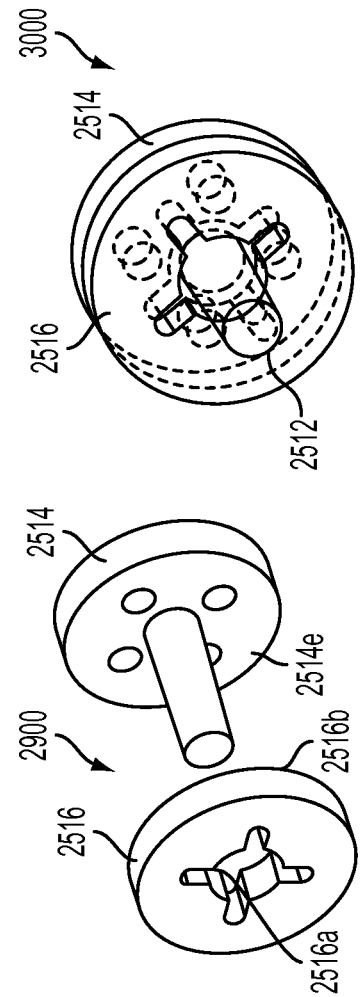

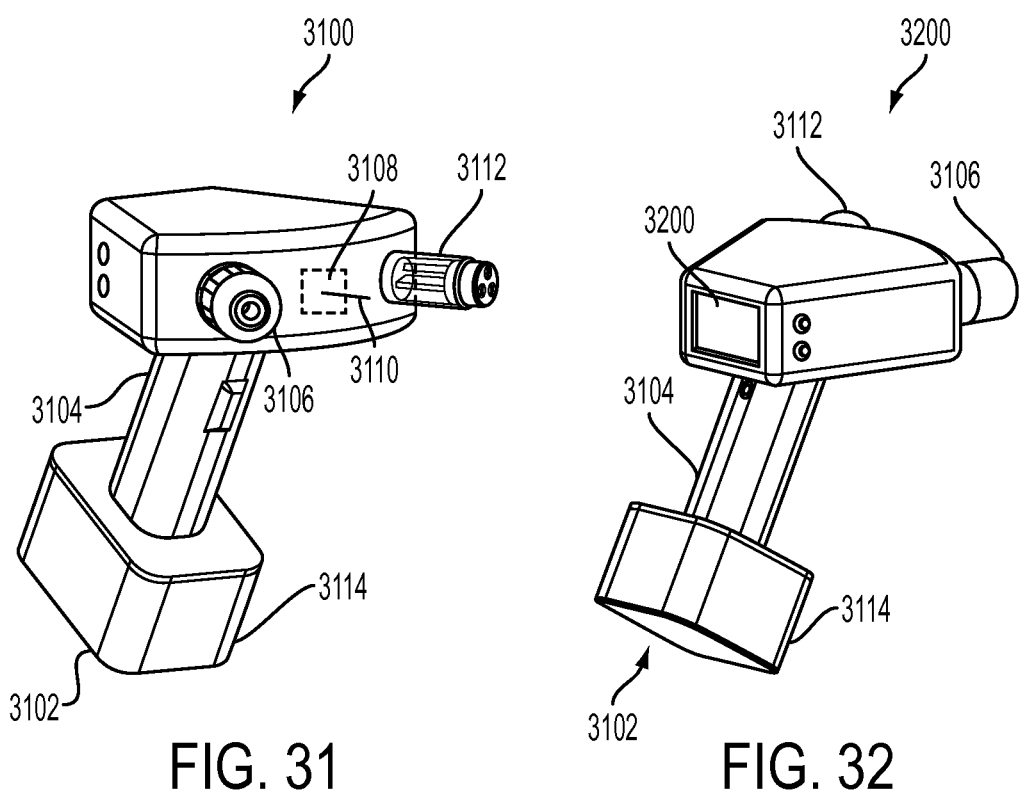

SYSTEMS FOR ELECTROCHEMICAL SORTING OF METALS AND ALLOYS

STATEMENT REGARDING FEDERALLY SPONSORED RESEARCH OR DEVELOPMENT

This invention was made with United States Government support under contract DE-AR0000405 ARPAE-METALS-PARSE, beginning on Feb. 3, 2014 awarded by the U.S. Department of Energy. The United States Government has certain rights in the invention.

TECHNICAL FIELD

The present disclosure relates generally to the field of metal and metal alloy identification, and more particularly to systems designed for electrochemical sorting or separating of metals and alloys.

BACKGROUND

Extracting metals from their ores is an energy intensive process. After extraction, the metals are commonly alloyed in different proportions to achieve certain physical or chemical characteristics. When the useful life of objects using these metals and alloys is over, they are typically sent to scrap yards and shredded to smaller pieces to be sold as aggregated scrap metals. Value of such aggregates is much lower compared to the fresh alloys, since they cannot be simply re-melted and re-used, due to their unknown composition. While lab methods such as atomic emission spectroscopy can identify each sample, the time taken for testing each sample may be several minutes, and requires sophisticated and expensive analytical tools. Therefore the cost of identification far outstrips the residual value of the scrap metal itself.

A large industry segment in the scrap materials business makes and uses machines that broadly separate some of the scrap components very fast, in matter of seconds. For instance, air-vortex separators remove plastics; Eddy-current separators remove glasses and plastics; Magnetic separators remove ferrous items; and X-ray assisted conveyor belts remove high atomic weight metals such as copper. However, within the same metal families, identifying and separating different alloys at a fast speed of seconds or less has been a challenge.

Several hand-held and portable instruments and technologies exist today that are capable of identifying different alloys, but they have not been integrated to high throughput conveyor-belt systems due to their slower speeds of 30 seconds to several minutes per test. Such technologies include: (a) X-ray fluorescence spectroscopy and (b) Laser-ablation spectroscopy, and variations and combinations of these. In X-ray spectroscopy, an X-ray beam excites the orbital electrons of the surface of the scrap sample, resulting in optical fluorescence. The fluorescence spectrum is measured by sensitive photo-detectors. Each metal has a characteristic spectrum, and by de-convoluting the spectrum, the metal components in the alloy can be determined. In Laser-ablation method, a very high power laser beam vaporizes a small amount of the surface of the sample, and an optical emission or absorption spectroscopy is done on the vapor to determine its composition. Both these technologies require 10-40 seconds to measure each sample, and cost between US$ 20,000 and US$ 40,000, making it prohibitive for implementation in conveyor-belt sorters. For such sorters, the identification must be made within a few seconds.

INCORPORATION BY REFERENCE

The disclosure of co-pending and commonly assigned U.S. application Ser. No. 14/576,309, filed Dec. 19, 2014, entitled, "Electrochemical Metal and Alloy Detector and Method", by Saroj Sahu et al.; and U.S. application Ser. No. 14/626,092, filed Feb. 19, 2015, entitled "Systems for Electrochemical Sorting of Metals and Alloys", by Craig Eldershaw et al., are each totally incorporated herein by reference.

BRIEF DESCRIPTION

Provided are systems for electrochemical sorting of different metals and alloys.

BRIEF DESCRIPTION OF THE DRAWINGS

FIG. 19 depicts a three test probe system and a scrap (common) electrode configured within a single compact body.

FIG. 20 is a cross section of FIG. 19.

FIG. 21 illustrates a further view of the concepts of FIGS. 19 and 20.

FIG. 25 illustrates an end portion of a test probe cartridge having a valving connection to control the movement of electrolyte to the membrane.

FIG. 26 shows a cross section view of FIG. 25.

FIG. 27 depicts the valving components of FIGS. 25 and 26.

FIG. 28 shows an alternative view of FIG. 27.

FIG. 29 depicts the components of FIGS. 27 and 28 in an exploded fashion.

FIG. 30 depicts an alternative view of the FIGS. of 27, 28 and 29.

FIG. 31 shows a first view of a handheld test sorter according to the present application.

FIG. 32 shows an alternative view to that of FIG. 31.

DETAILED DESCRIPTION

Among other aspects, the present systems employ:
1) Electrolytes (e.g., water-based electrolytes) that are capable of a reversible redox reaction with the metal and its alloy components are employed. It is noted that a cation of the electrolyte consists of a metal ion having at least two redox states that are soluble in the electrolyte medium.
2) An asymmetrical excitation charges and discharges the redox reaction rapidly and in such a manner that the net amount of electric charge (Coulombs) transacted to a sample is zero.

Figure 1:
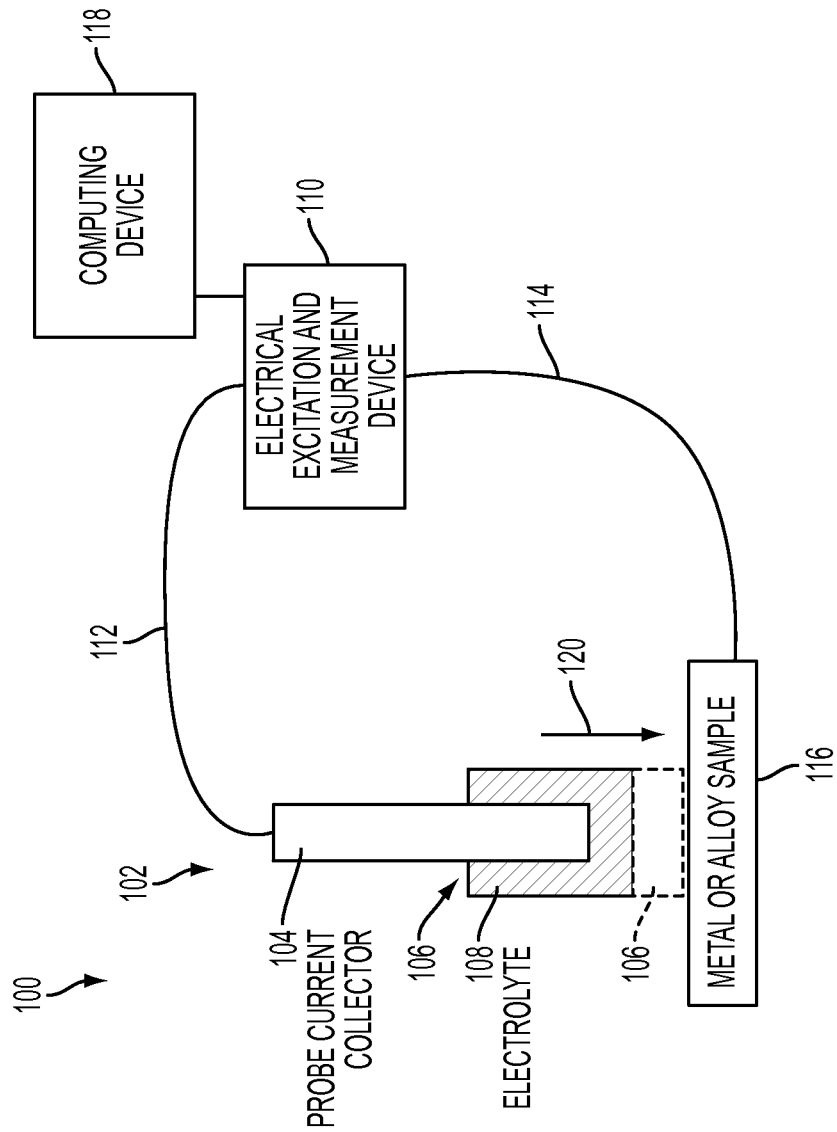
FIG. 1 illustrates an electrochemical probe based testing system according to the present application.

An arrangement 100 for testing samples consisting of different metals and metal alloys according to the teachings of the present application is shown in FIG. 1.

A testing system 102 of arrangement 100 includes a current collector probe 104, with a non-electrical conductive component (such as a membrane) 106 containing an electrolyte 108, and an electrical excitation and measurement device 110. The testing system further includes an electrical connection line 112 in operative electrical connection with the probe 104 and the electrical excitation and measurement device 110, and an electrical connection line 114 at one end in operative electrical connection to the electrical excitation and measurement device 110. The other end of electrical connection line 114 is positioned to be in operative electrical connection with sample 116 which is to be tested. Also provided as part of the test system 102 is a computing device 118 to record and/or store measured values (voltage and/or current) measured by the measurement portion of electrical device 110, and to perform operations to look-up or otherwise calculate and/or associate the recorded and/or stored measured values with previously known values that are characteristics of specific metals and/or metal alloys.

The probe 104 is formed of an appropriate material including but not limited to glassy carbon, graphite, carbon-plastic composite, other forms of carbon, a various metals, including, metal oxides, a metal salts or metal salt composites (e.g., Tin, Lead, and Indium) that form galvanic coupling through the electrolyte with the sample 116. The probe 104 may also be made from other materials including but not limited to chalcogenide. The membrane 106 is in certain embodiments a porous or fibrous polymeric material with open pores. In other embodiments the membrane is a non-porous ion exchange membrane. The membrane is, in certain embodiments configured in, but not limited to, a planar form, such as to cover just the bottom surface of the probe, while in other embodiments the membrane is formed as a sleeve with a bottom surface (e.g., a "cup" shape) that covers the end portion of probe 304 and well as a certain amount of the sides of the probe. Still further, in other embodiments the membrane is replaced with a meniscus as the component located between the probe 104 and the sample 116.

Arrow 120 of FIG. 1 indicates the movement direction of the probe 104 for operative contact between the probe 104, membrane 106 (with electrolyte 108), and sample 116, whereby an ionic path is formed. The operational contact being shown by dotted line connection to "106". In other embodiments it is the sample that is moved to the probe, and in still further embodiments both the probe and the sample are moved to make contact The movements being made by use of known technology. Measurements are capable of being made by the electronic device 110, with or without excitations from the electronic device 110 during the measurement operation.

Figure 2:
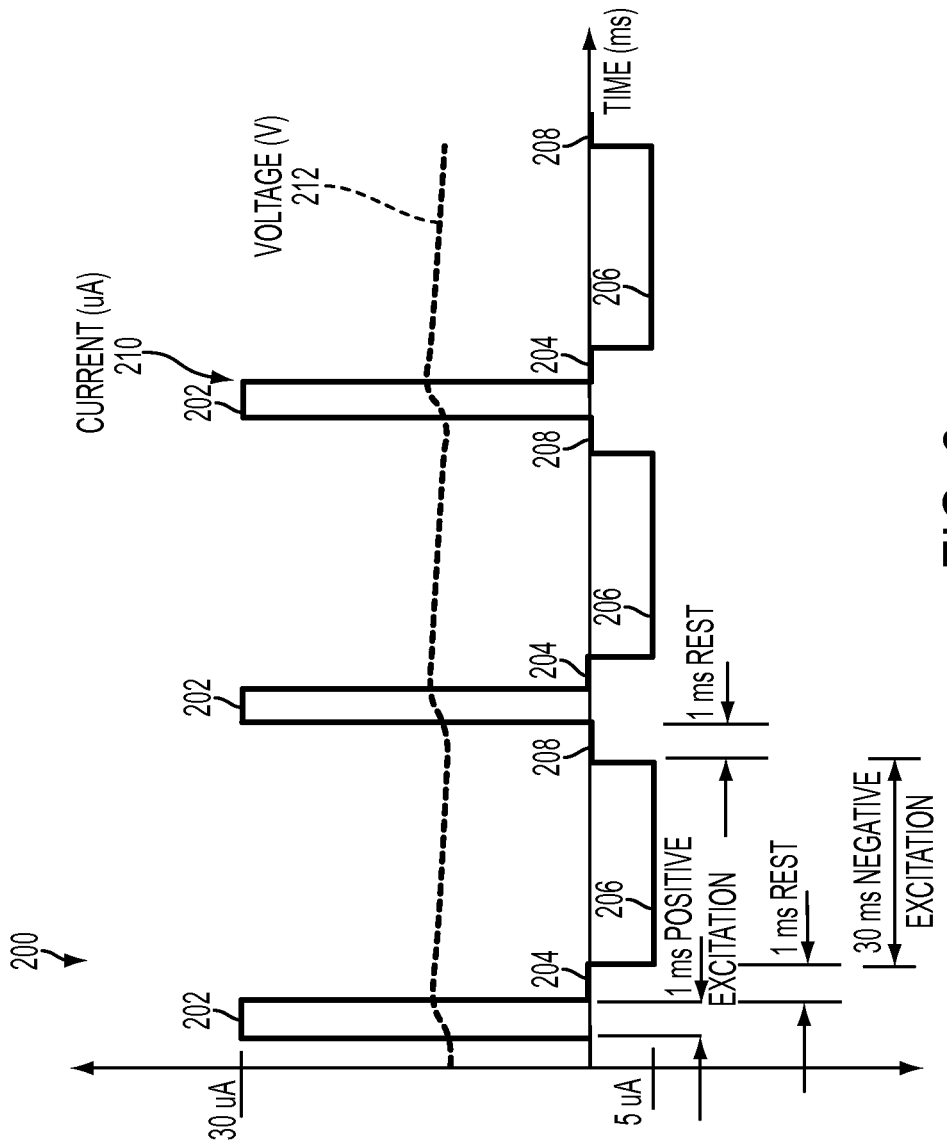
FIG. 2 is a plot showing asymmetric current excitation and resulting voltage response for the test system of FIG. 1.

Turning now to FIG. 2, excitations generated by the excitation portion of the electrical excitation and measurement device 110 of FIG. 1 is described in graph 200. In this disclosed embodiment, the described excitation sequence is followed—
I. Positive current of 30 uA for 1 mSec from probe into the sample metal/metal alloy (202).
II. Zero current (rest time) for 1 mSec (204).
III. Negative current of 5 uA for 30 mSec from metal into the probe (206).
IV. Zero current (rest time) for 1 mSec (208).
In this embodiment this sequence is repeated for 10 times (shown repeated three times in FIG. 2), and the output may then be averaged.

The plot of the value of the current as a function of time is shown by solid line 210.

While this sequence is running, the potential is measured via electrical device 110 of FIG. 1 as a function of time and recorded. The plot of the potential as a function of time is shown as the dotted line 212.

The pulse sequence of FIG. 2 is now explained in more detail. Technically, when one metal is brought into electrolytic contact with another metal, or more generally, when a conductor electrolytic and another conductor are brought into contact, there is no electron transfer, but there is ionic transfer, and a potential will exist. This potential is used to represent characteristics of the two metals. However, if there is no significant current being generated, a small amount of impurity in the system substantially changes the output being observed. For example if there is pure aluminum on one side, and pure graphite on the other side, but there is even a speck of impurity (such as iron), since there is no significant current flow, the iron acts to destabilize the output readings, meaning the sample metals cannot be reliably identified.

To address this issue, as shown in FIG. 2, current based cycle pulsing is provided for generating charging and discharging operations (which means the cycle pulsing is acting as a battery). Therefore, the relative magnitude of the metals or the composition of the metals is far more important than the impurities (e.g., the speck of iron). So impurities on the sample (e.g., aluminum) have a negligible effect on the testing operations (e.g., the voltages that are observed).

One reason the excitations being used are asymmetric is that (as in most batteries), charging is much more efficient than discharging. So the charging pulse is able to use a narrow pulse for a short time to achieve the desired results. The discharging cycle pulsing is selected with a current and time so that substantially the same number of electrons is extracted from the sample that were added during the charging operation. Discharging is normally slower than charging. Therefore more time is given to complete the discharge of the electrons, which again will result in substantially a net zero electron exchange (e.g., no net electrons are input to the sample) during one full pulsing cycle of FIG. 2.

A second reason the charging time is held short is to avoid the charging operation from generating a gas discharge, which could occur in some implementations with an extended charging time period.

The described pulsing sequence minimizes the impact of impurities on the sample being tested, by providing a current flow, while at the same time ensuring that a net zero exchange of electrons occur.

In the embodiment shown in FIG. 2, three full pulsing cycles (202-208) are depicted, each having: a charging period of one millisecond (202), a first rest period of one millisecond (204), a discharge period of 30 milliseconds (206), and a second rest period of one millisecond (208). For a total cycle of 33 milliseconds.

It is to be appreciated, these time periods and pulsing values are for a particular embodiment, and there can be applications where different time periods and values are to be used. In other embodiments, the charging operation may be anywhere in the range from 0.5 milliseconds up to 5 seconds. Similarly, the discharge may be anywhere in the range from 3 milliseconds to 30 seconds, and the rest periods from 0.5 milliseconds to 5 seconds. The actual selected time periods may be any within these selected ranges in accordance with a particular application. Additionally, current values may also vary dependent upon particular implementations of the system, such as anywhere in the range of 3 uA to 300 uA for the positive charging pulse and −0.5 uA to −50 uA for the discharging pulse, as long as the concept of having a substantially no net electron transfer once the entire pulsing cycle has been completed is maintained.

Further, while the discussion in connection with FIG. 2 indicted the use of ten cycles of each pulsing sequence (202-208), dependent upon the implementation as little as one pulsing cycle may in some embodiments be useful and in others, two or more pulsing cycles may be appropriate for the particular implementation.

It is noted however, that when large values are used, for example if five-second charge and 30-second discharge sequences are used the voltage swings will become larger, since as charging is taking place the voltage goes up, and as discharging, is occurring the voltage goes down, so having a longer duration in terms of charging and discharging, then the pulsing cycle (in the form of the saw-tooth waveform) would be fairly wide. Whereas, in the case of the 1 millisecond and 30 millisecond situation, the voltage line 212 is substantially flat, as shown in FIG. 2, which improves the ability to ensure substantially no net gain of electrons on either side. The present embodiments are using a charge balance technique.

Also, an aspect of the present disclosure is the speed at which the readings can be taken by the electronic device 110 of FIG. 1. Thus, the narrower the pulse width in the saw tooth wave arrangements, the faster the readings can be obtained. Thus using the values of FIG. 2, a testing operation to determine the identity of a specific sample would be:

1 Msec+1 Msec+30 Msec+1Msec=33 Msec×10 cycles=330 Msec

Turning to a particular implementation, the inherent chemical reaction in the ionic process by a system such as system 100 of FIG. 1, in the case of using Ferric Chloride electrolyte for a Copper (Cu) sample can be written as follows—

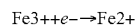

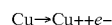

Cu, for instance, is the major alloy component for the 2xxx series of aluminum alloy. The amount of copper will therefore determine the average potential observed during the excitation.

Although copper is shown here as an example of the redox reaction, other metals undergo similar redox reactions and may therefore be identified with empirically determined voltage values.

Also, while this disclosure focuses it examples on identification of different aluminum alloys, other metals and metal-alloy systems, such as steel, bronze and gold systems can be identified with this method by an appropriate choice of electrolytes.

Figure 3:
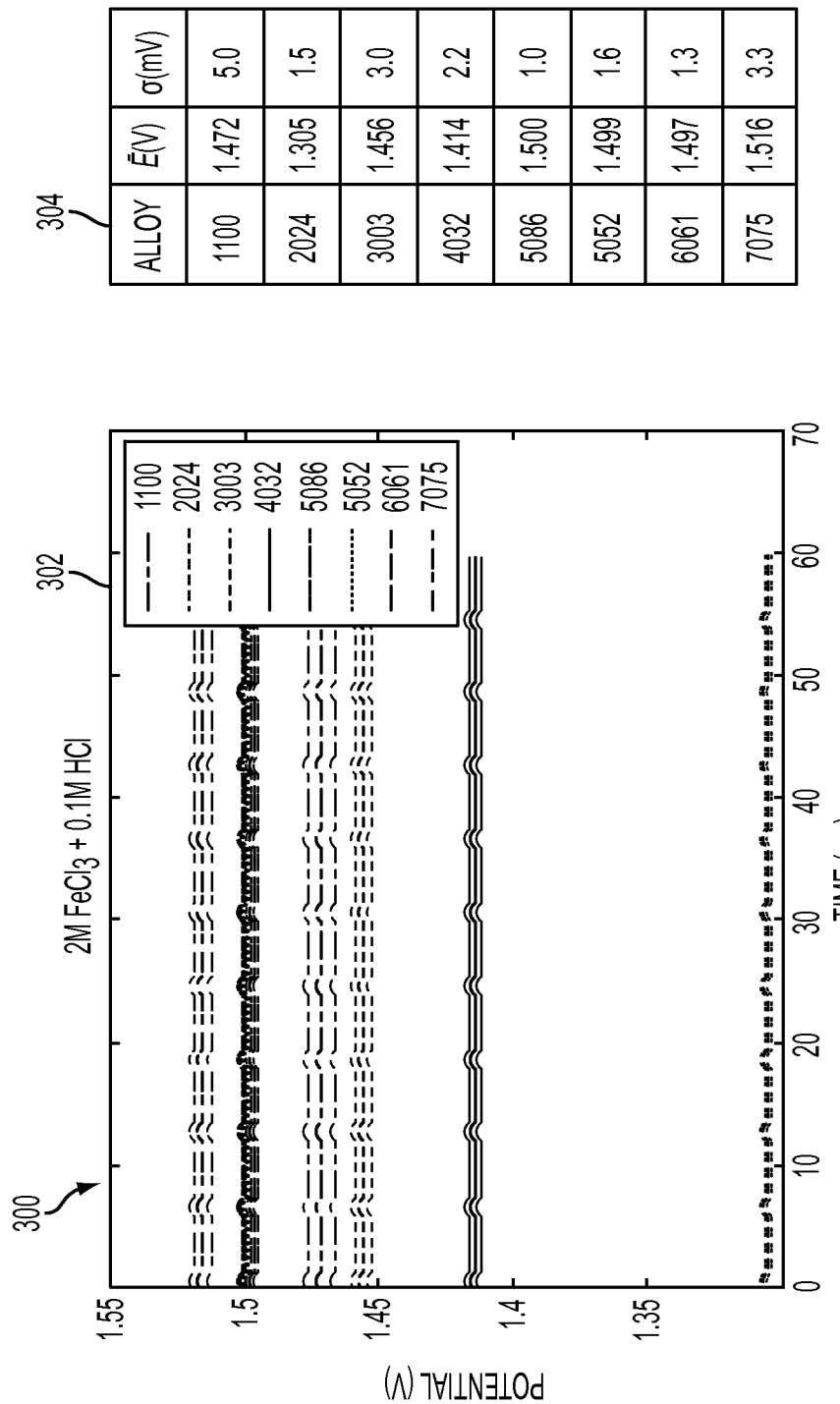
FIG. 3 is a plot graph and table showing measurement of voltage as a function of time with asymmetric alternating current excitation using Ferric Chloride electrolyte for different aluminum alloy compositions.
Figure 4:
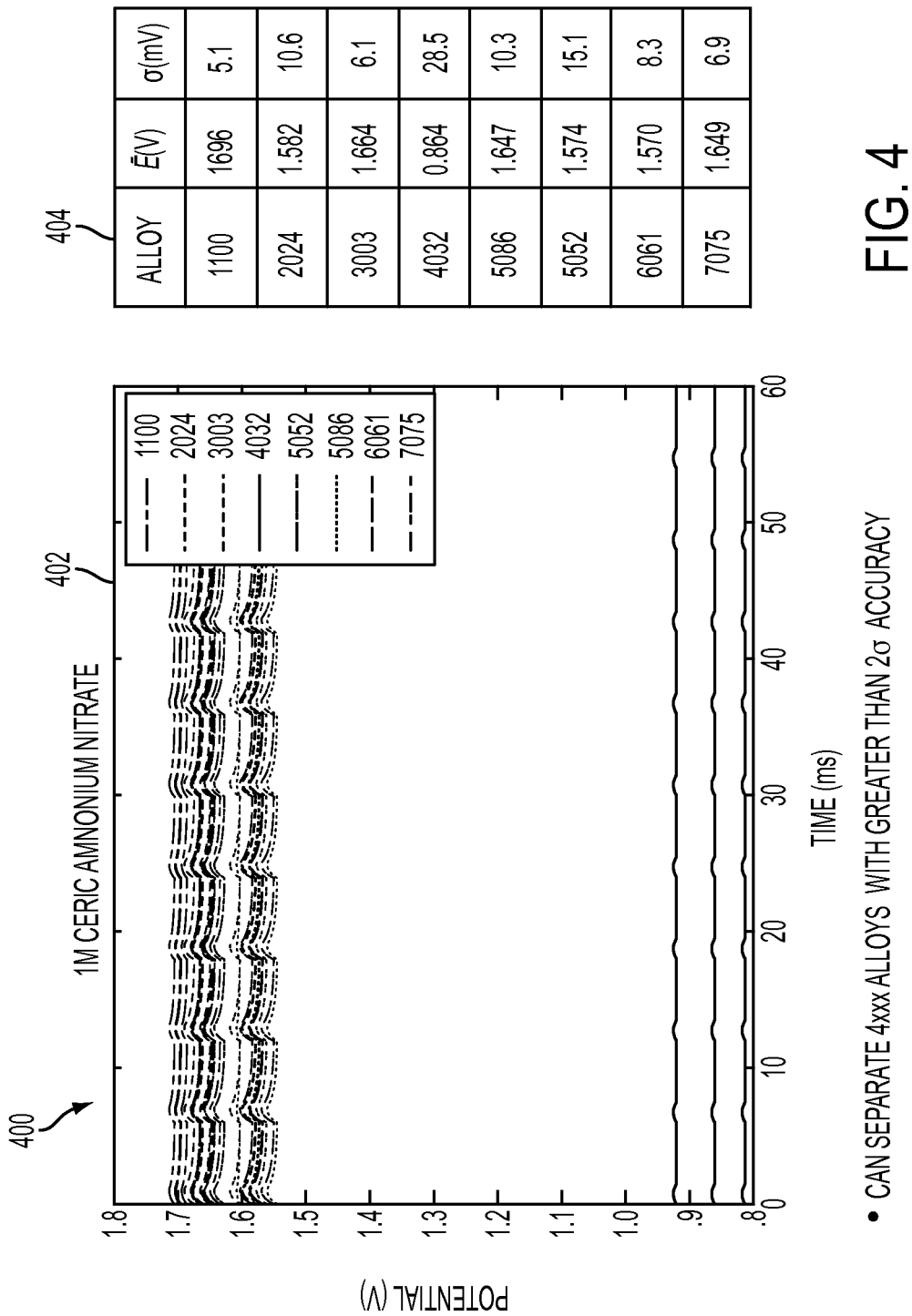
FIG. 4 is a plot graph and table showing measurement of voltage as a function of time with asymmetric alternating current excitation using Cerium Ammonium Nitrate for different aluminum alloy compositions.
Figure 5:
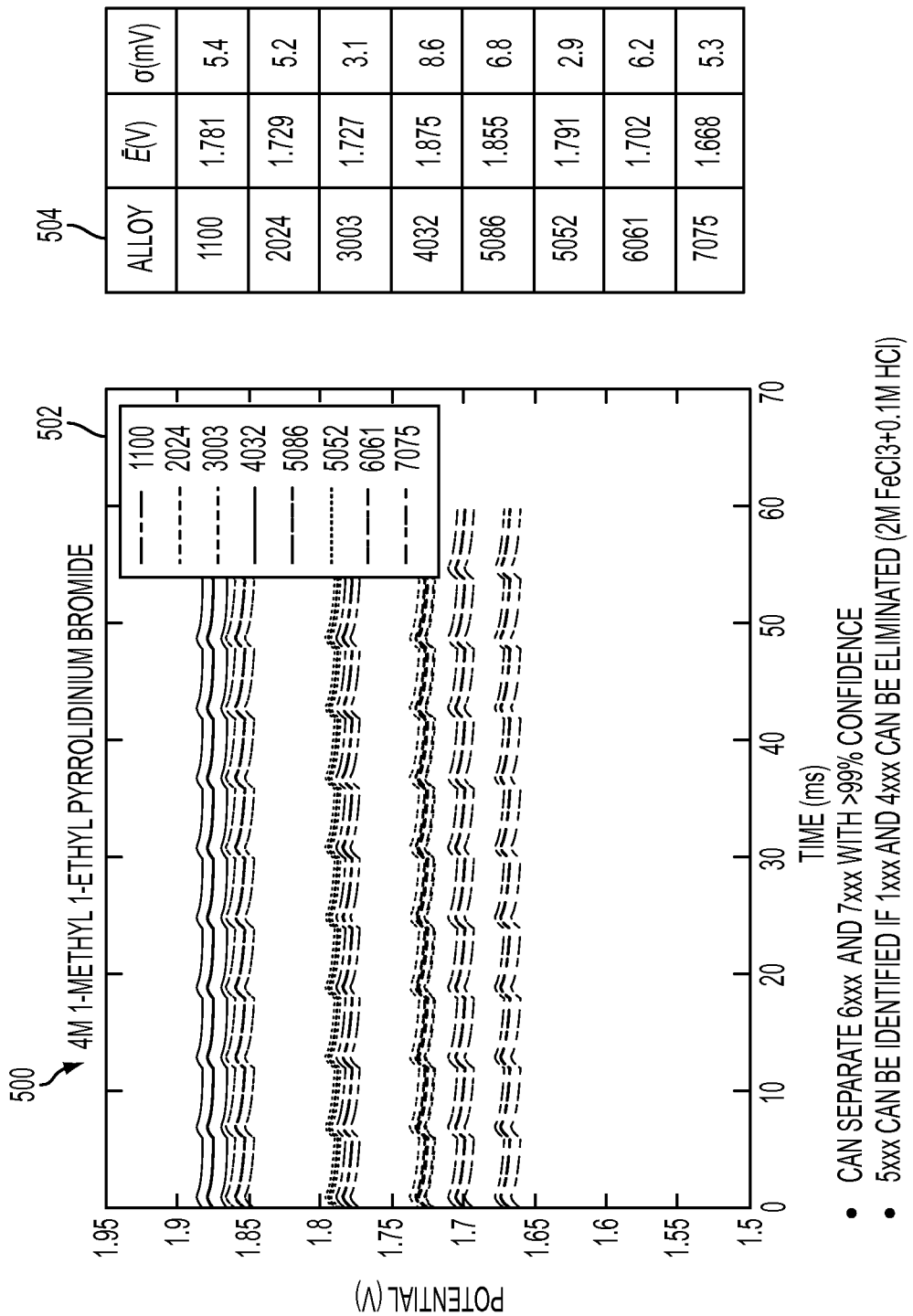
FIG. 5 is a plot graph and table showing measurement of voltage as a function of time with asymmetric alternating current excitation using 1-methyl 1-ethyl pyrrolidinium bromide electrolyte for different aluminum alloy compositions.

Using a testing system based on the teachings of FIG. 1, attention is now directed to results of testing operations as illustrated in FIGS. 3, 4 and 5.

Turning now to FIG. 3, the potential observed as a function of time for a Ferric-Ferrous system using Ferric Chloride electrolyte, for different Aluminum alloys is shown in illustrations 300, including graph plot 302 and corresponding table 304. It may be observed that while alloys 2024, 4032, 7075, and 3003 are clearly identified with widely separated voltages, alloys 5086 and 5052 are substantially indistinguishable from each other. However, the family of 5xxx alloys is distinguished from other alloys of table 304.

The above observations are shown in both plot graph 302 and table 304. More particularly, with attention to table 304, in the left-most column are the particular metal alloys being tested (1100, 2024, 3003, 4032, 5086, 5052, 6061 and 7075). The middle column lists the voltage readings (E (V)) for corresponding identified metal alloys, and the right most column lists the related sigma (σ) value (i.e., standard deviation values) of the test results for each of the noted alloys. More particularly, the sigma value represents the accuracy of the measured voltage values for corresponding samples. For example, when the separation of two alloy's average measurements is 3.0 σ or greater then the accuracy of the identification is greater than 99%. For 2.0 σ or greater separation, the accuracy of the test results is understood to be approximately 92% accurate. On the other hand, test results for alloys 5086, 5052, and 6061 of table 304 were found to be substantially indistinguishable from each other having their average less than 2σ apart, therefore considered not reliable.

It is considered that a testing system using one electrolyte may not be able to distinguish all the alloys or metals in a given family, depending on the metal or alloy under investigation. In that case, a different electrolyte with the same excitation method would provide a different set of voltages, thus providing an orthogonal set of measurements.

For instance, illustrations 400 of FIG. 4, including a graph plot 402 and table 404 show test voltage results for different aluminum alloys for a testing system using a ceric ammonium nitrate electrolyte. Cerium has two redox states: +3 and +4. The correspondent reaction may then be—

$$Ce4++e-\rightarrow Ce3+$$

$$Cu\rightarrow Cu++e-$$

As can be observed, using this electrolyte, and the same testing system and excitation method shown in FIGS. 1 and 2, it is possible to separate the 4xxx aluminum alloy family quite well.

This electrolyte is sensitive to the surface oxides of the metals and alloys. Table 404 of FIG. 4 illustrate, as reflected in the sigma (σ) column of table 404 that only 4xxx series alloys have sigma (σ) values that have a 2σ or greater separation.

Turning now to FIG. 5 illustrations 500 include a graph plot 502 and table 504 of voltages for different aluminum alloys with 1-methyl-1-ethyl pyrrolidinium bromide (4M MEP Br) used as the electrolyte. In this case, the redox reaction is—

$$Br-\rightarrow Br+e-$$

$$Cu++e-\rightarrow Cu$$

Similar to FIGS. 3 and 4, table 504 includes the voltages (E(V)) and the a values (mV), for a number of alloy metal groups. In table 504 it is illustrated that the testing results of the present system are able to separate 6xxx and 7xxx with over 99% confidence (i.e., 3.0 π or greater). Whereas the alloy group 5xxx can be identified if 1xxx and 4xxx are eliminated (e.g. using a second test with 2M FeCl3+0.1 M HCl as the electrolyte).

Figure 6:
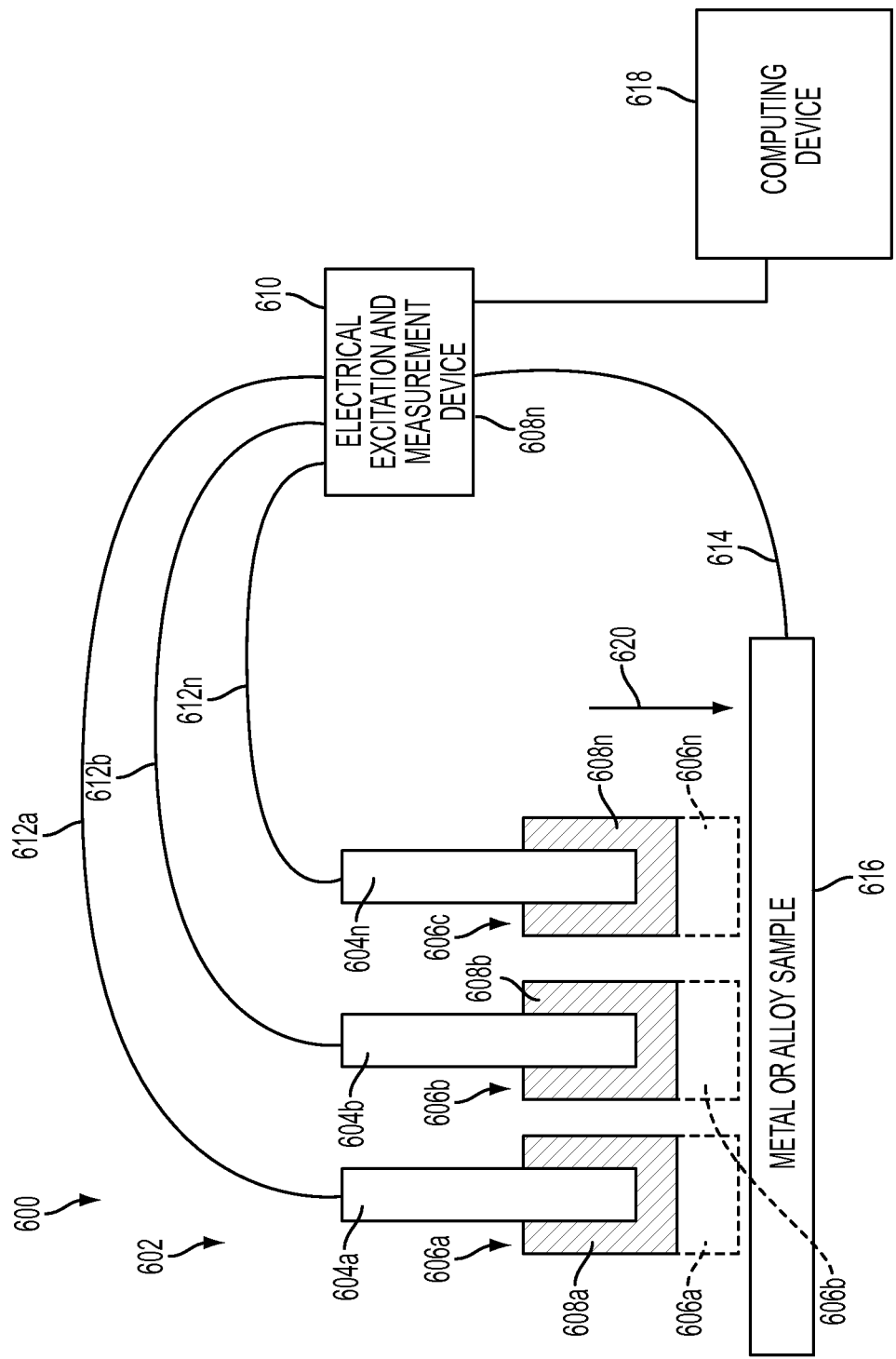
FIG. 6 illustrates an electrochemical probe based testing system according to the present application.

Turning now to arrangement 600 of FIG. 6, depending on the samples and range of identification and accuracy required, one or multiple electrolytes may be used in the identification problem. In FIG. 6, depicted is a multi-probe test system 602, having multiple current collection probes 604a, 604b, 604n and corresponding non-electrical conducting components (e.g., membranes) 606a, 606b, 606n with different suitable electrolytes 608a, 608b, 608n. These probes can probe a piece of metal at the same time or in sequence, and/or probe different samples in parallel. Test system 602 further includes an electrical excitation and measurement device 610 (such as electrical device 110 shown in FIG. 1), electrical connection lines 612a, 612b, 612n in operative connection with corresponding probes 604a, 604b, 604n and the electrical excitation and measurement device 610, and an electrical connection line 614 extending and in operative contact to the electrical excitation and measurement device 610 at one end. The other end of electrical connection line 614 is in operational electrical contact with the sample 616 to be tested. Also provided as part of the testing system 602 is a computing device 618 to record the values measured by the measurement portion of electrical device 610, and to perform operations to look-up or otherwise calculate and/or associate the recorded measured values with pre-determined values that are associated with specific metals and or metal alloys, such as shown in FIGS. 3, 4, 5.

A look-up table, stored for example on computing device may be used to classify the alloy or metal into different categories. The look-up table is established empirically by measuring known reference metal and/or metal alloy compositions. The computing device 618 (and 118 of FIG. 1) in certain embodiments is a computer, laptop, electronic pad, handheld or other smart electronic devices. In other embodiments the computing device is an electronic device dedicated to the present operations. The computing device includes a memory for storing software and/or a lookup table to perform operations to correlate the detected voltage and/or current values to empirically determined voltages that represent specific metals and/or metal alloys.

As similarly illustrated in FIG. 1, an arrow 620 shows a movement direction of probe 604 which provides operational contact between the probe 604, membrane 606 (with electrolyte 608), and sample 616, by which an ionic path is formed. The operational contact being represented by dotted connection lines for "606a", "606b" and "606n". In other embodiments it is the sample 616 that may be moved to the probe, and in still further embodiments, both probe and sample are moved to make contact. The movements being accomplished by known control technology.

The probe and non-electrically conductive component arrangements of FIG. 6 may be used to individually probe different samples sequentially and/or in parallel. Alternatively, more than a single probe may be used to probe the same sample. The probe/non-electrically conductive component arrangements may use the same electrolyte, or different electrolytes for different ones of the probe/non-electrically conductive component arrangements. For example, when the more than a single arrangement is used to test the same sample each arrangement may have a different electrolyte. Using different electrolytes, will for certain implementations, provide a more detailed and/or reliable identification of the sample.

Figure 7:
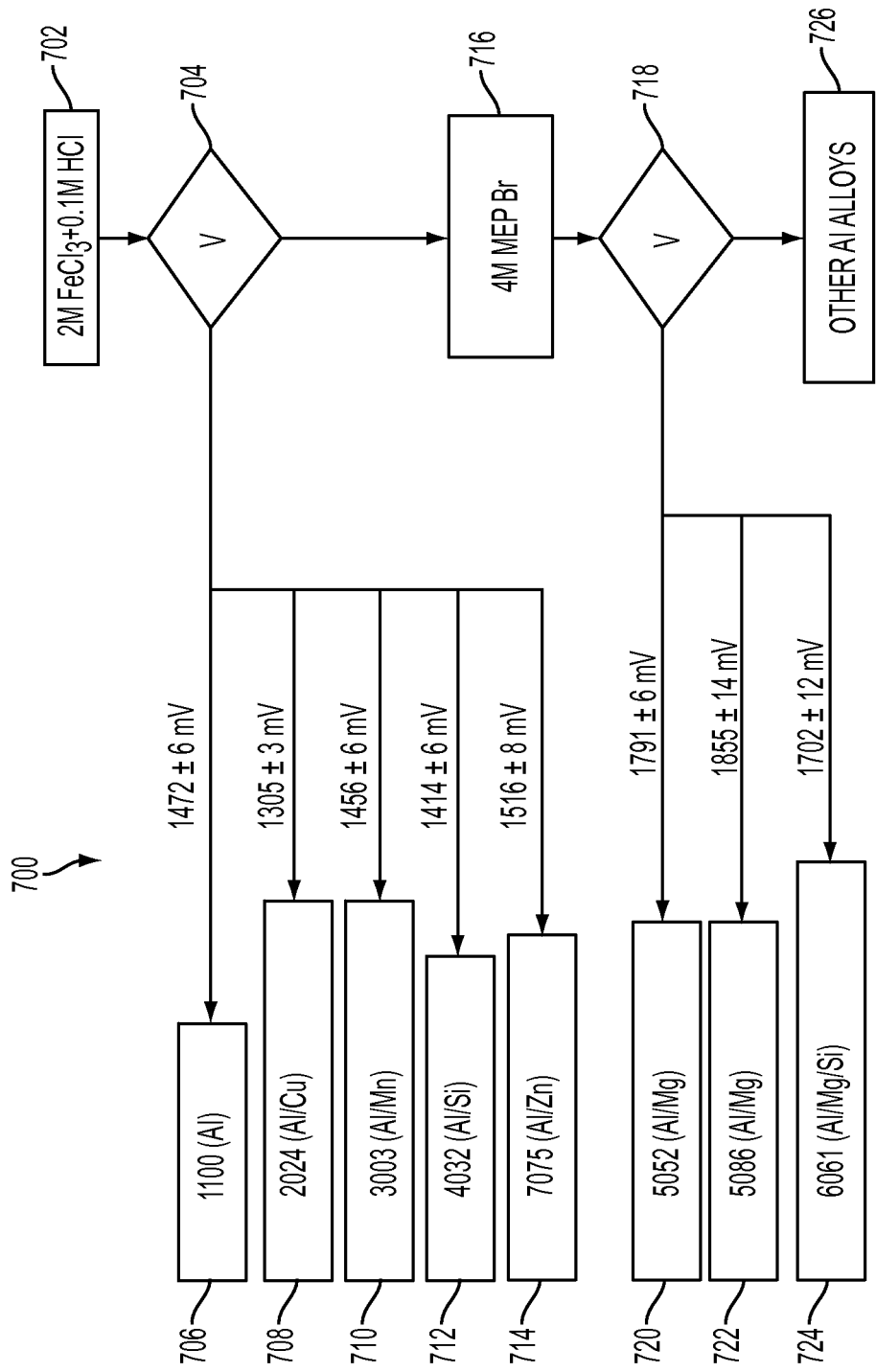
FIG. 7 is a flow chart algorithm to identify different aluminum alloys using asymmetric current excitation and two probes using two different redox electrolytes.

Turning to FIG. 7, depicted is a flow chart 700, which may be used to generate an algorithm (software) for use with computing device 618 of FIG. 6, for identifying/separating a variety of aluminum alloys (where one sample at a time is tested in accordance with flow chart 700) using two different electrolytes for different probe/non-electrically conductive component arrangements. FIG. 7 represents a flow chart for 95% accurate sorting of aluminum alloys, one alloy at a time. Accordingly, the ranges are reported as +2σ value. Initially, a first electrolyte (2M FeCl3+0.1M HCl) represented at block 702 is used in electrochemical test system (e.g., 602 such as described in FIG. 6). In initial testing (block 704) the electrolyte of block 702 is used in the testing of samples (i.e., where one sample is under test at a time) identified by blocks 706, 708, 710, 712, and 714, where the samples are unidentified at the time of testing. The millivolt potentials (1472+/−10 mV, 1305+/−3 mV, 1456+/−6 mV, 1414+/−6 mV, 1516+/−8 mV) that are obtained for the respective samples (boxes 706-714) are correlated to previously identified voltages that are characteristic of corresponding metals/metal alloys (in this example aluminum/aluminum alloys), including aluminum and aluminum alloy groups 1100, 2024, 3003, 4032, 7075.

The previously mentioned characteristic voltages, in one instance are found by empirical observation of known metals/metal alloys. These characteristic voltages are sorted in a look-up table, or used as part of an algorithm, or in other manners that allow for a matching of the measured voltage value(s) to the known characteristic voltage value(s), such as in a computing device described in FIG. 6.

FIG. 7 includes a second electrolyte (4M MEP Br) used with a separate probe/non-electrically conductive component arrangement (block 716). In initial testing employing these systems the second electrolyte is used to obtain voltage(s) as designated by diamond (V) 718 for a plurality of metallic samples. The obtained voltages 1791+/−6 mV, 1855+/−14 mV, 1702+/−12 mV, are again correlated to specific aluminum and/or aluminum alloys 5052, 5086, 6061, shown by blocks 720, 722, and 724 respectively. Block 726 acknowledges that the systems described herein may be used with other electrolytes to identify additional metals/metal alloys. Of course the exact voltages may vary with the precise formulation, age, or temperature of the electrolyte and other variables apparent to one skilled in the art.

Figure 8:
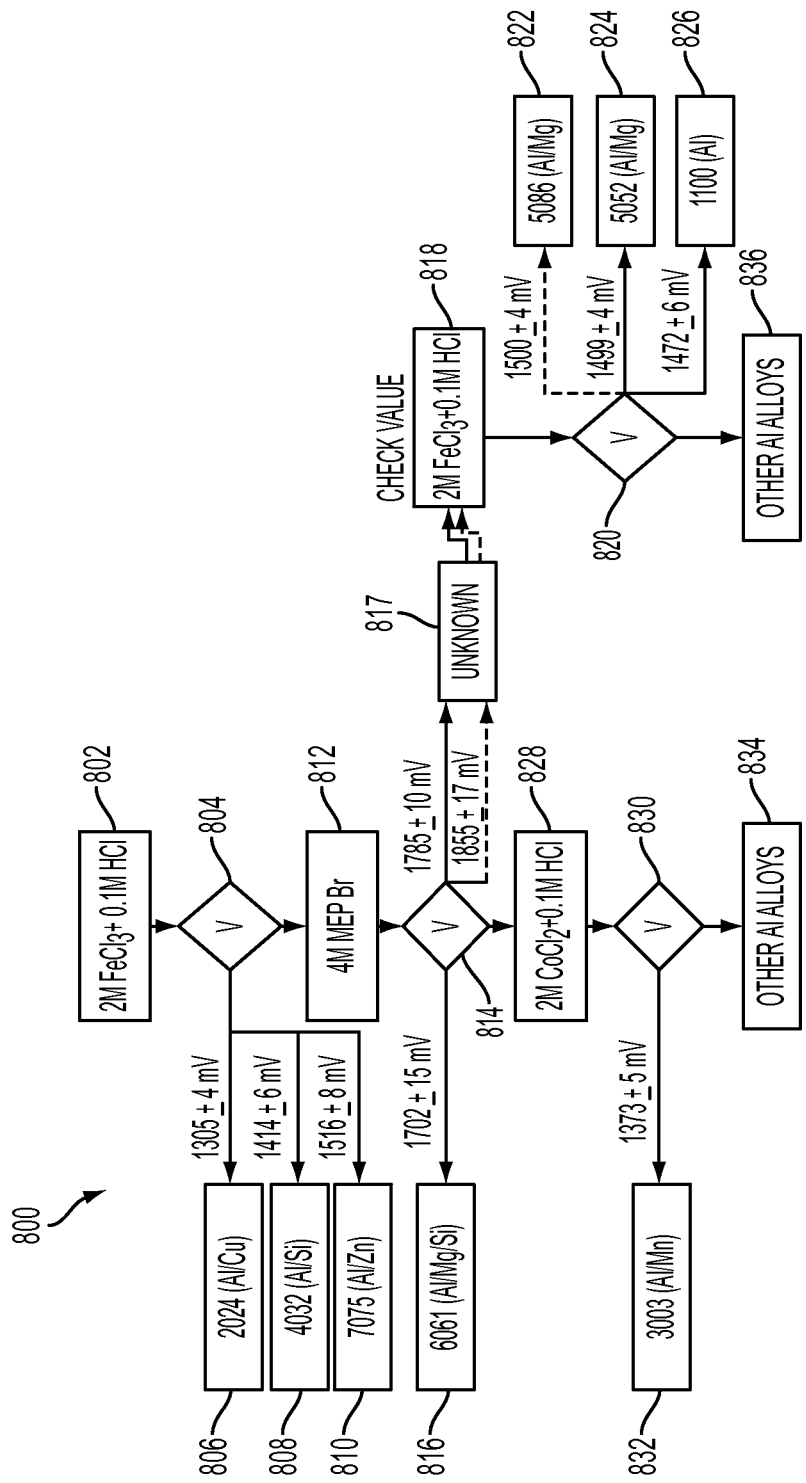
FIG. 8 is a flow chart algorithm to identify different aluminum alloys using asymmetric current excitation and three probes using three different electrolytes.

Shown in FIG. 8 is a flow chart 800 for separating a variety of aluminum alloys based on a look up table or other correlation mechanism, using three electrolytes.

Initially, an electrolyte (2M FeCl3 0.1M HCl) in box 802 is used in a test system, such as test system 602 of FIG. 6, where the testing operation "V" (diamond 804) is used to test samples (i.e., again, where one sample is under test at a time) 806, 808, 810, the metallic content of which is not known at the time of testing. The testing operation 804, results in the generation of specific millivolt potentials (respectively, 1305+/−4 mV, 1414+/−6 mV, and 1516+/−8 mV). These measured values are then correlated to voltages values that are known to be characteristic of specific metal compositions (e.g., 2024 (Al/Cu), 4032 (Al/Si), 7075 (Al/Zn)). Thus the testing operation identifies previously unidentified metal samples.

FIG. 8, includes another electrolyte 4M (MEP Br) box 812, used as described above in a testing (evaluation) operation "V" (diamond 814), for a sample 616, having an unknown metal content. Using the electrolyte and testing operations described herein, the unidentified sample causes a millivolt potential of 1702+/−15 mV to be generated. This voltage potential is then correlated to previously empirically identified voltages corresponding to characteristics of certain metal compositions (i.e., 6061 (Al/Mg/Si)).

FIG. 8 also shows the use of multiple probes with different electrolytes testing the same unknown metal sample in order to more definitively define that unknown sample. More particularly, returning to step 812, a probe having 4M MEB Br electrolyte, performs an evaluation at step (diamond) 814 on an unknown sample 817. Dependent upon the characteristics and/or composition of the unknown sample 817, a voltage 1785±10 mV or 1855±19 mV is detected by probing operations. It is to be understood that these values are selected as examples only and that if sample 817 had other metal characteristics still other voltages would be returned. Therefore, it is to be appreciated that while unidentified sample 817 is shown once as a single box, the single box is intended to represent the possibility of different metallic sample compositions for the purposes of this discussion. With this understanding, this example explanation will be continued. So when the voltage 1855±17 mV (dotted line) is detected, a preliminary identification has occurred (Aluminum Alloy 5086), but the user may wish to verify this identification. Therefore, a next step is to again review the voltage reported from 802 (which used an electrolyte of 2M FeCl3+0.1M HCl) and check this sample (check value box) 818. Then, as further comparisons are made with respect that sample 817 at evaluation step (diamond) 820 and a voltage of 1500±4 mV is determined, this voltage is correlated with a known metal composition, i.e., 5086 (Al/Mg). In other words, box 822 has verified the preliminary sample identification of box 817.

The second part of this discussion (i.e., dealing with the voltage 1785±10 mV) returned by testing sample 817 results in a failure to identify a particular metal composition. Then, similar to the previous discussion, a further review the voltage reported from 802 (which used an electrolyte of 2M FeCl3+0.1M HCl) is used in an evaluation operation (diamond) 820. In this situation, if the sample in box 817 returns a voltage of 1499±4 mV, then it is correlated to 5052 (Al/Mg) as shown in box 824. Similarly, if the evaluation returns a voltage of 1472±13 mV, it can be determined that the sample 817 is the aluminum metal 1100 (Al) of box 826.

The foregoing discussion is intended to show that a single sample may be tested by more than one probe, having different electrolytes. This multi-probing process narrows down the possibilities to more specifically identify an unknown metallic sample.

Still further FIG. 8 includes electrolyte (2M CoCl2+HCl) box 828, used in a testing operation "V" (diamond 830), for an unknown sample 832. The results of the testing operation results in a millivolt potential measurement of 1373+/−5 mV, for the metal sample 832. This voltage value is then found to correlate to a specific metal—3003 (Al/Mn). FIG. 8 further shows other Al alloys may also be tested for by use of an appropriate electrolyte (boxes 834, 836).

The forgoing examples have described electrical excitation and measurement devices, 110, 610 as a single unit diagram. It is to be understood these functions maybe accomplished by separate device such as a signal generator, a voltmeter and ammeter, among other appropriate electronic devices.

Figure 9:
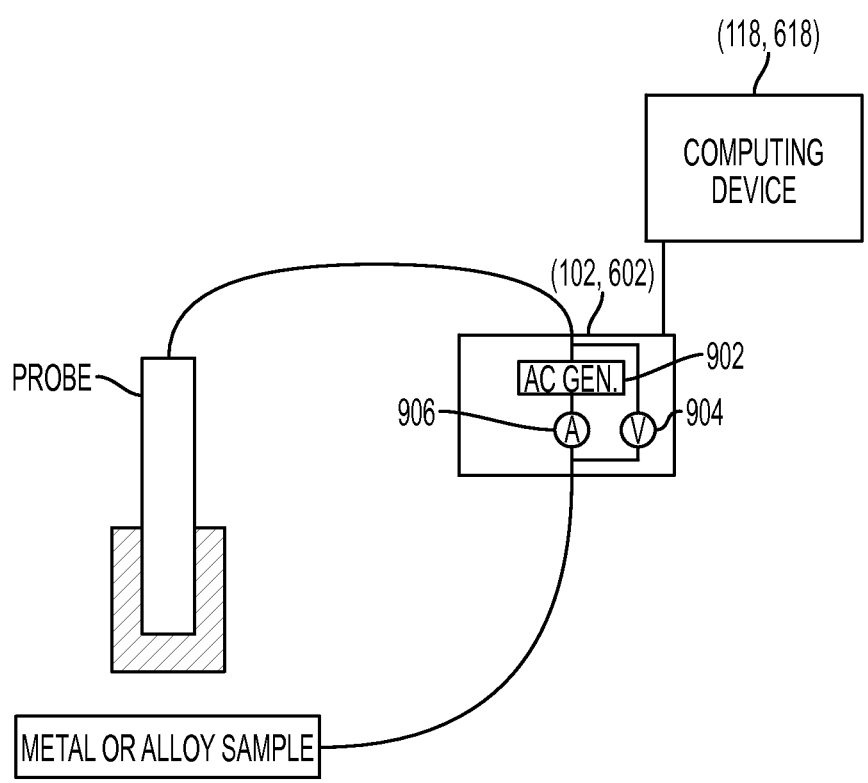
FIG. 9 provides a more detailed view of the electrical excitation and measurement device described in FIGS. 1 and 6.

Turning more particularly to FIG. 9, a more detailed view of the electrical excitation and measurement devices (102, 602) of the present disclosure (as shown in FIGS. 1 and 6) is provided. In one embodiment the electrical excitation and measurement device (102, 602), may consist of an AC current generator 902, a voltmeter 904, and an ammeter 906. The output of the voltmeter 904 and/or the ammeter 906 being provided to the computing device (118, 618 of FIGS. 1 and 6 respectively).

Figure 10:
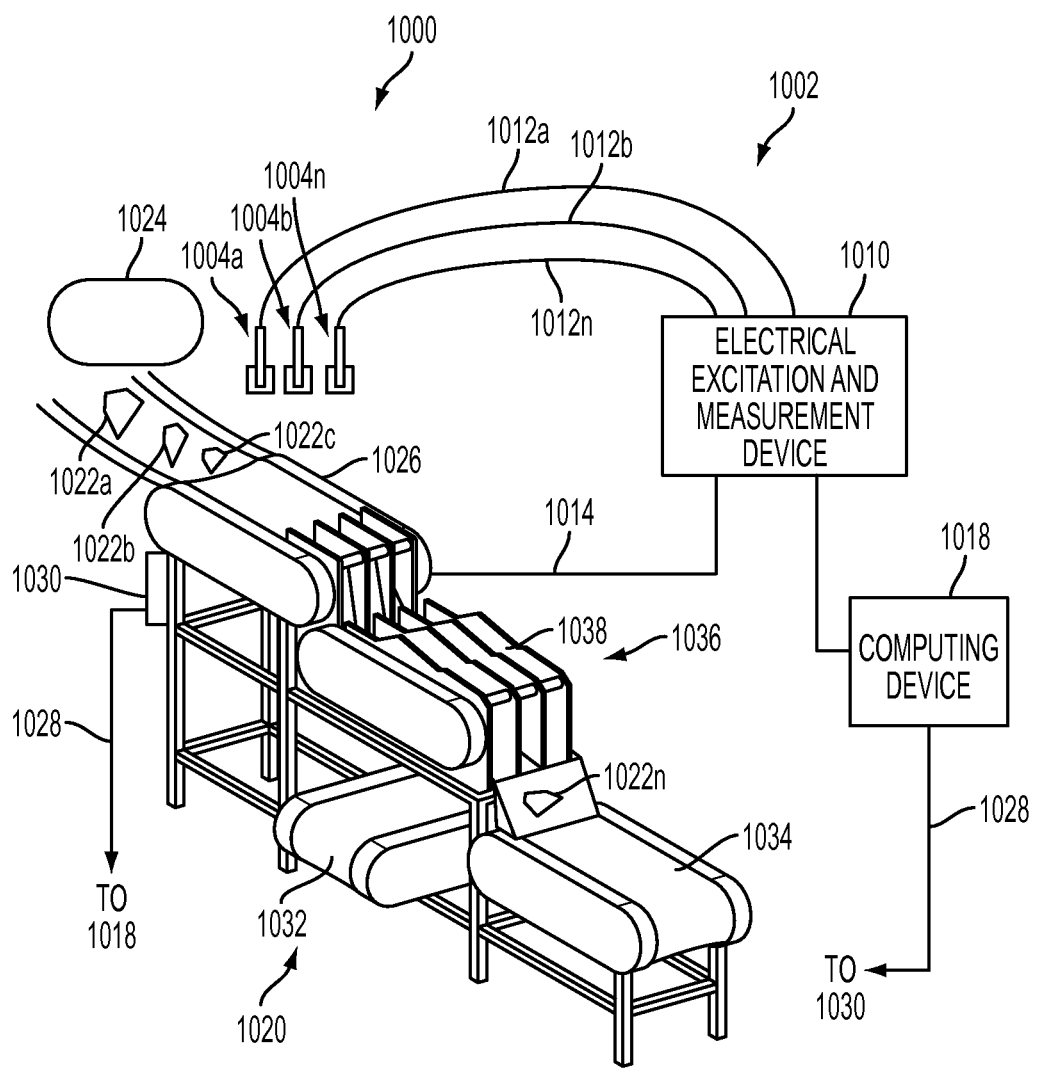
FIG. 10 illustrates the present concepts employed in connection with a conveyer system.

Turning to FIG. 10, illustrated is metallic sample identification system 1000 including a probe based electrochemical testing system 1002, such as has been previously described, in connection with FIGS. 1 and 6. The system 1002 includes metal probe arrangements 1004a, 1004b and 1004n, electrical excitation and measurement device 1010, electrical connectors 1012a, 1012b, 1012n and 1014, and computing device 1018. The electrochemical probing system 1002 is now shown in association with a conveyor system 1020 on which are metal samples 1022a, 1022b, 1022c and 1022n. System 1000 of FIG. 10 also includes a cleaning arrangement 1024, wherein the metal samples may be cleaned prior to be being probed by the probing system 1002.

It is known that in many situations, the metal or alloy sample being interrogated or tested may have dirt, paint or oxidation on its surface. Before the probes are used, the sample surface can be cleaned. The cleaning may be done in one or more of the following ways by an appropriately employed treatment system, as represented by system 1024:

I. A milling arrangement for milling a small portion of the sample surface.

II. An abrading arrangement for abrading the sample surface with a metal brush or with electro-chemically non-active sand-paper—such as Tungsten carbide papers.

II. A chemical cleaning arrangement for chemically cleaning the sample surface of the metal, such as with phosphoric acid.

It is to be noted that in testing system 1012, the probe arrangements 1004a-1004n are located near a first level 1026 of the conveyor system 1020. The probes may be arranged in such a way as to be controlled to be brought into contact with the metal samples as they are passing, such that testing is an ongoing rapid testing process. The conveyer system 1020 includes a controlled power system, such as a single or multiple motors to move the conveyor belts at a predetermined speed, where this speed is synchronized with the operational capabilities of the test system 1002. It is to be appreciated that while the probes are shown associated with the first level conveyor 1026, probes may be located at different locations of the conveyor system and are shown at the first level 1026 simply for convenience. Also, in one embodiment the electrical connector 1014 is electrically associated with the first conveyor system by a "streetcar" type connection. By streetcar connection it is meant that it is held in contact with the conveyor belt such that an electrical connection is maintained as the conveyor belt moves. It is of course to be appreciated that other electrical connections may be used.

Thus, in this system metallic samples (e.g., scrap metal) are carried on the conveyer belt system 1020. Then the probes (with electrolytes) are brought into operational contact with various ones of the metallic samples, resulting in a voltage potential generated not by connecting to the directly (e.g., metal to metal) but through the electrolyte. However, the electrical connection of electrical connector 1014 provides a metal-to-metal connection between the metallic samples 1022a-1022n and the conveyor belt (for example, upper level portion 1026), where no electrical potential will exist between the electrical connection of the electrical connector 1014 and the metal sample(s) 1022a-1022n on the surface of the conveyor system 1020. Therefore the measurements being made by the testing system 1002 are not affected by the metal to metal connection (i.e., metal samples and metal conveyor belt) in determining the identification of the particular unknown samples on the conveyer belt system 1020.

Another aspect of the present disclosure has computing device 1018 in communication with conveyor system 1020, via line 1028, which is in operative connection with a controller/motor component 1030. In one embodiment once computing device 1018 has operated to correlate data readings (e.g., voltage values) from electrical excitation measurement device 1010, to identify the type of metal or metal alloy of a particular sample, the computing device outputs this information to controller/motor component 1030, which in turn sorts the identified sample to a particular area of the conveyor system. For example, the movement of the metal or metal alloy causes the identified sample to be processed to either lower conveyor system portion 1032 or 1034, by movement of redirector mechanisms 1036 of middle conveyer system portion 1038 controlled by controller/motor component 1030.

Electrolyte Holders or Carriers

The foregoing discussion has disclosed certain aspects of electrochemical metal and alloy composition detection. The following now discloses particular implementations to accomplish such detection.

As illustrated in FIGS. 1 and 6, electrically conductive (also described as current conductive) test probes (e.g., 104 of FIG. 1, 604a, 604b, 604n of FIG. 6) are associated with certain types of electrolytes (e.g., 108 of FIG. 1, and 608a, 608b, 608n of FIG. 6), where the electrolytes are carried by non-electrical conducting components (e.g., membranes 106 of FIG. 1, and 606a, 606b and 606n of FIG. 6). In one embodiment, the membranes have previously been described as non-porous ion exchange membranes that are in a planar form such as to cover just the bottom surface of the probe, while in other embodiments, as shown in the figures, the membranes are formed as a sleeve with a bottom surface (e.g., a cup shape). While these designs are desirable for certain embodiments, in other embodiments where, for example, the metals or alloys being tested have debris contaminated surfaces (e.g., containing oil, dirt particles, metal shavings, etc.), it is beneficial that any debris from the surface of the metal and/or alloy samples which may become trapped in the electrolyte carrier (e.g., membrane), will not interfere with the testing operations.

It is understood, the electrolyte in the testing systems is in an operational circuit between the test probe (as called system electrode) and the metal or alloy (also at times the common electrode). However, any other electrical connection between the test probe and the metal or alloy being tested can result in degradation of the testing operations. Therefore, it is desirable that potentially conductive debris, such as metal shavings, not be located with or near the testing circuit to effect proper testing of the metal or alloy. A simple solution would be to dip both the test probe (system electrode) and the metal or alloy into a bath of electrolyte. A drawback is this solution is that it would waste a large amount of electrolyte (that comes away with the metal or alloy), it may easily contaminate the electrolyte, and it may be dangerous and cumbersome to implement.

Figure 11:
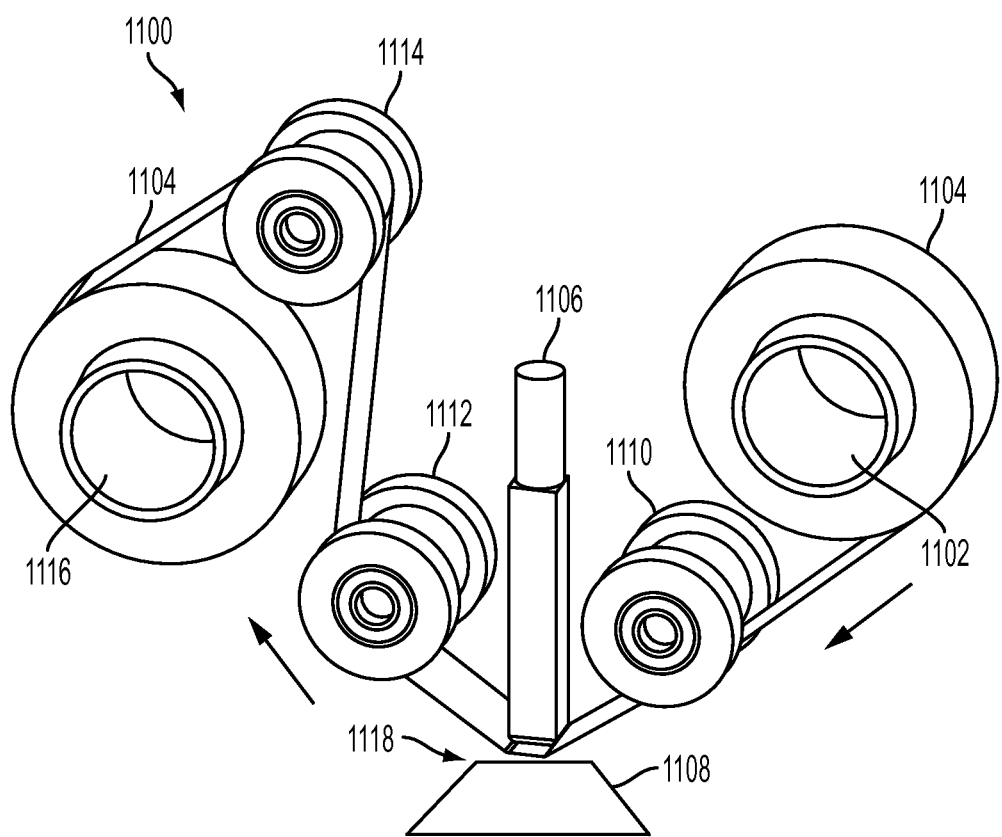
FIG. 11 illustrates a roll-to-roll implementation of the membrane being used between the test probe and metal or alloy samples being tested.

Therefore, it is considered desirable to provide an electrolyte holder for use in environments where debris exists. One such type of electrolyte holder is shown in FIG. 11. Electrolyte holder 1100 includes a feed roll 1102 holding of a non-conductive wicking material (e.g., membrane) 1104 that has been soaked in an electrolyte and positioned to be placed in operative physical connection with both the test probe 1106 and the metal or alloy 1108. In this embodiment membrane 1104 carried on feed roller 1102 is moved through intermediate rollers 1110, 1112, 1114 until it reaches a take-up roller 1116. As shown in FIG. 11, electrical probe 1106 (similar to the probes of FIGS. 1 and 6) is placed above a surface of membrane 1104, whereby the membrane 1104 is positioned between electrode probe 1106 and the piece of metal or alloy 1108 to be tested. In this embodiment, as the test probe 1106 moves toward metal or alloy 1108, the membrane 1104 is intermediate, such that an ionic path is formed in a manner similar to that discussed in connection with FIGS. 1 and 6. By the design and operation of electrolyte holder 1100, any debris (including metal shavings) that might have transferred from the surface of the test probe 1106 or metal or alloy 1108 during a previous testing operation is moved away from the testing area 1118 as the membrane 1104 is taken up on take-up roller 1116. In one embodiment, the membrane 1104 may be a woven cloth tape (for example, JNJ Industries' 401 under stencil wipe) comprised of a hydroentangled blend of 55% cellulose and 45% polyester. In one embodiment such a membrane tape has a thickness of approximately 0.3 mm, and therefore would have a low electrical resistance.

Thus by the described design, a fresh piece of the membrane (i.e., cloth or fabric tape) is easily and automatically moved into service. This movement is again beneficial when/if the electrolyte becomes contaminated, such as if a particle of metal or alloy from one sample gets embedded in the membrane, potentially interfering with readings of subsequent samples. Movement of the membrane 1104 may occur after every sample measurement, after a fixed number of measurements, or when an algorithm controlling movement indicates that the system is becoming degraded (i.e., possibly through periodic checks against a known metal or alloy).

Turning to a second embodiment, although the embodiment of FIG. 11 teaches that pieces of metal or alloy fragments embedded in the membrane is no longer in the series circuit of the testing area 1118, embedded metal or alloy fragments on the downstream side of the membrane may still be electrically connected to the test probe 1106 electrode through the membrane (e.g., cloth or fabric tape) 1104 that is wet with conductive electrolyte. Also, the used or contaminated electrolyte from the downstream could potentially move (through capillary motion) to the active testing region 1118. If the testing system is sufficiently sensitive, this becomes an issue. Therefore, in environments where such issues may arise, a further embodiment of an electrolyte holder is shown in FIG. 12, as electrolyte holder system 1200.

It is noted this figure is a simplified version of a roll-to-roll system shown, for example, in FIG. 11. In FIG. 12, a feed roller 1202 holds a certain amount of an electrolyte membrane tape 1204, which moves as shown in the direction of arrow 1210 to a take-up roller 1208. Similar to the discussion with FIG. 11, a current collector test probe 1206 is positioned over a piece of metal or alloy (e.g., scrap metal or alloy) 1212. The membrane tape 1204 is positioned in between these two components, again, in a manner similar to that described in FIG. 11. However, a difference between the membrane tape 1104 (FIG. 11) and the membrane tape 1204 of the present embodiment is that instead of being homogenous, the tape 1204 is composed of an alternating series of connected panel sections of absorbent material 1204a, 1204c, 1204n, and non-absorbent material 1204b and 1204d. Motion of the tape 1204 is controlled in such a way that test probe 1206 is always over an absorbent electrolyte filled segment (1204a, 1204c, 1204n) during actual testing, and this segment has no electrical or capillary connection with any used segment (i.e., 1204n marked with a slashed circle). Particularly, non-absorbent segments 1204b and 1204d do not carry any electrolyte, and therefore a buffer or separation section is provided such that electrical connections are not inadvertently created. It is to be appreciated that while some of the sections of membrane tape 1204 may appear to be physically spaced from and not touching other sections, it is understood that the sections are formed as a continuous tape 1204. For example, in one embodiment the sections are associated with a backplane carrying all the panels, and in other situations each of the sections are placed immediately adjacent such as shown by 1204b and 1204c.

Figure 12:
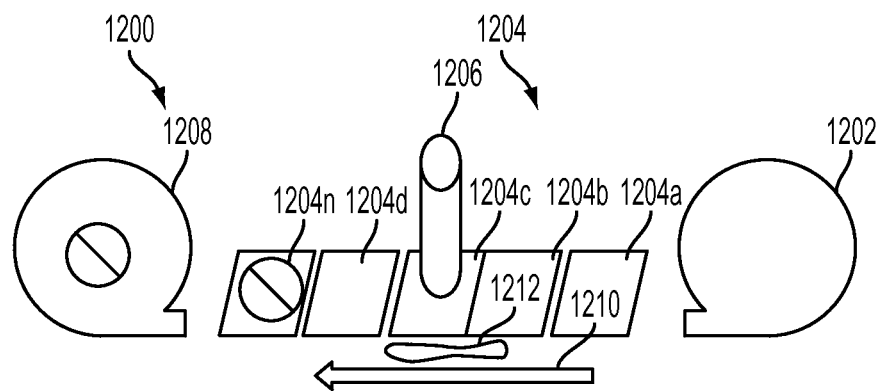
FIG. 12 depicts a similar roll-to-roll concept of FIG. 11 wherein the membrane tape includes alternating absorbent and non-absorbent sections.

These above-noted roll-to-roll systems of FIGS. 11 and 12 allow for automatic and frequent changes of the membrane for the different testing operations.

The electrolyte can be delivered to the membrane tape in a number of ways, such as a fresh spool of fabric may be presoaked, the electrolyte might be dipped onto the membrane tape just prior to reaching the area of the test probe. The electrolyte may also be dripped onto the test probe (or the metal or alloy), among other ways that would be apparent to one of ordinary skill in the art.

Figure 13:
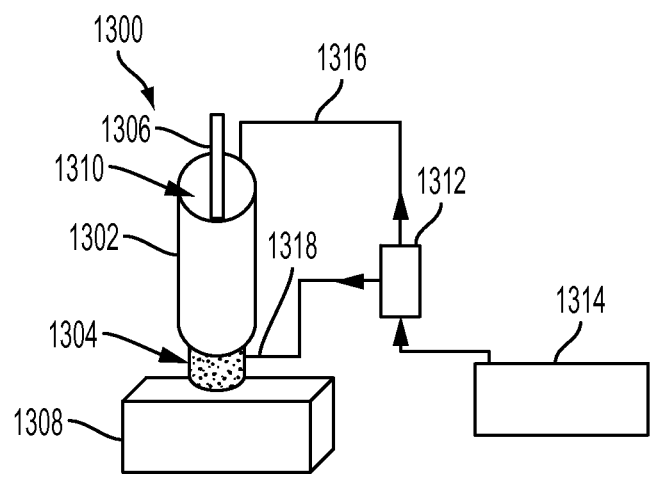
FIG. 13 depicts an electrode test probe arrangement including a tube and porous tip member.

In addition to the roll-to-roll systems of FIGS. 11 and 12, an alternative arrangement to ensure a clean membrane is being employed is to use a replaceable porous tip type electrolyte arrangement. This is shown, for example, in porous tip arrangement 1300 of FIG. 13. As illustrated in this simplified illustration, porous tip arrangement 1300 includes a hollow-type tube 1302 which at a bottom end is covered by a porous membrane portion 1304. Within tube 1302 is a test probe 1306 similar to that discussed in connection with the preceding figures. As shown in FIG. 13, the porous membrane 1304 is in contact with a piece of metal or alloy (e.g., a scrap piece of metal or alloy in some embodiments) 1308. In one embodiment, the hollow tube 1302 is filled with an electrolyte 1310, which maintains the porous membrane 1304 soaked with the electrolyte such that a proper ionic circuit connection is made. In an alternative embodiment, the interior of tube 1302 may be filled with a porous material (similar to the material of the porous membrane 1304 or other sponge like material) which has absorbed the electrolyte 1310, allowing the electrolyte to seep into the porous membrane 1304 in a measured manner. In the embodiment where the tube 1302 is filled with electrolyte, test probe 1306 is immersed into the electrolyte. The lower opening of tube 1302 is plugged with the mentioned membrane tip 1304. In operation, the electrolyte wicks through the pores of the porous membrane tip 1304, enabling the necessary connection between test probe 1306 and the metal or alloy 1308. In this embodiment, the membrane tip 1302 is removable such that it may be replaced when it becomes contaminated, such as with metal or alloy shavings. The replacement operations may be done manually or automatically (such as with pick-and-place type machinery).

While in FIG. 13, the tip porous membrane 1304 is shown in a substantially circular configuration, it is understood the tip 1304 may take different shapes, porosities, materials and treatments. The optimal choice depending on issues such as the specific electrolyte chosen and desired probe size. In one particular embodiment may be a 3 mm thick piece of porous polyethylene with 20 µm pores, and treated so as to be hydrophilic.

In certain embodiments, the tube 1302 need not be filled with electrolyte; rather the electrolyte may be fed in by an off-board pump 1312 from an off-board reservoir 1314 and input line 1316, at such a rate that the membrane tip 1304 is maintained as wet, without completely filing the tube 1302.

To decrease the number of changes of the tip, an arrangement may be provided to clean the porous tip 1304 with continuous or occasional larger volumes of fluid such as from pump 1312, reservoir 1314, and input line 1316. Alternatively, a separate similar such system providing a specific type of cleaning fluid, such as through a cleaning line 1318 directly to the exterior of the porous tip 1304. Each cleaning system or process designed to remove contaminated electrolyte or debris from the surface of tip 1304. For more sensitive systems or those involved with more heavily soiled material (i.e., metal or alloys), the system may combine a large flush operation with a wiping operation to follow (i.e., manual or automated). It is to be understood that other non-conductive materials and structures could be employed (for example, the fibrous material such as the nib of a marker pen, or a sponge) as would be obvious to one of ordinary skill in the art. Further, the concepts of FIG. 13 may also be applied as part of a cartridge as discussed in more detail in connection with FIGS. 23 and 24.

Metal or Alloy Sample (e.g., Scrap) Used as an Electrode

Figure 14:
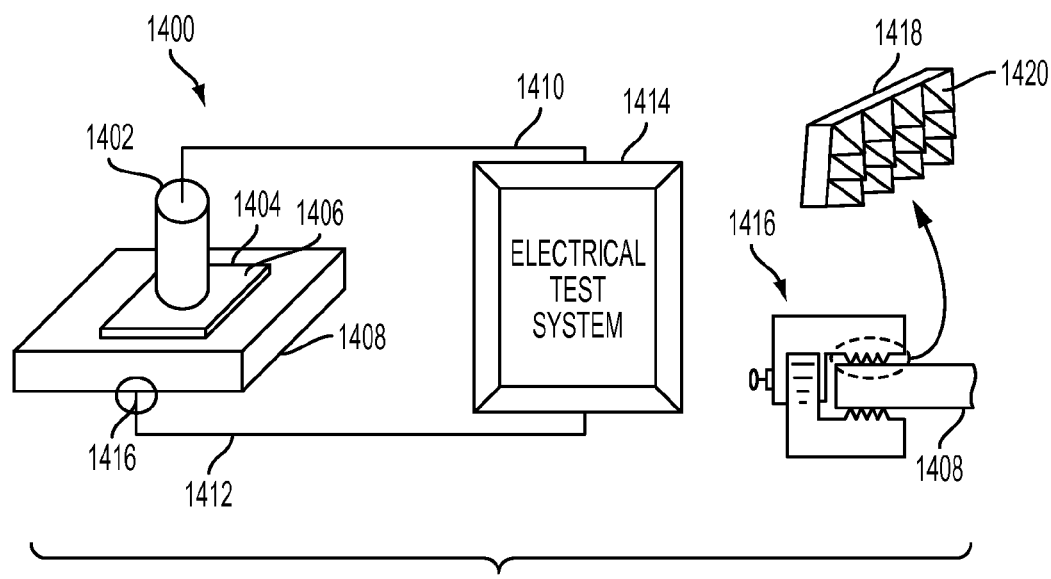
FIG. 14 illustrates a simplified version of a testing system using the metal or alloy scrap as an electrode.

The previous discussion described how, as shown in FIG. 14, testing system 1400, includes a test probe 1402, membrane 1404 carrying an the electrolyte 1406, and a metal or alloy sample (scrap) 1408, are used to form an ionic circuit (in the form of an electrochemical cell). As described, the metal or alloy 1408 itself is the other electrode of the formed electrochemical cell, which is connected, via electrical connection lines 1410 and 1412, to electrical test system 1414. This section describes embodiments as to how electrical connections (i.e., 1416) are made to the metal or alloy 1408.

The metal or alloy 1408 (when an aluminum or aluminum alloy) will often have a thin layer of aluminum oxide (other oxides for other metals or alloys), and possibly other insulators such as oil or paint on its surface. It may be necessary to penetrate through these insulators to the fresh metal or alloy in order to obtain a good electrical connection. This is often the case in bulk sorter type of environments. A particular embodiment to obtain a metal or alloy penetrating connection is to use a vise 1416 having at least one serrated jaw 1418 on the vise that holds the metal or alloy sample (scrap) 1408. One example of such a pattern is shown in the exploded view of a serrated jaw 1418. The hard sharp teeth 1420 of the pattern of the serrated jaw 1418 will bite in through the surface contamination to reach the bare metal or alloy. By this action a direct electrical connection to the vise or clamp completes the connection.

Figure 33:
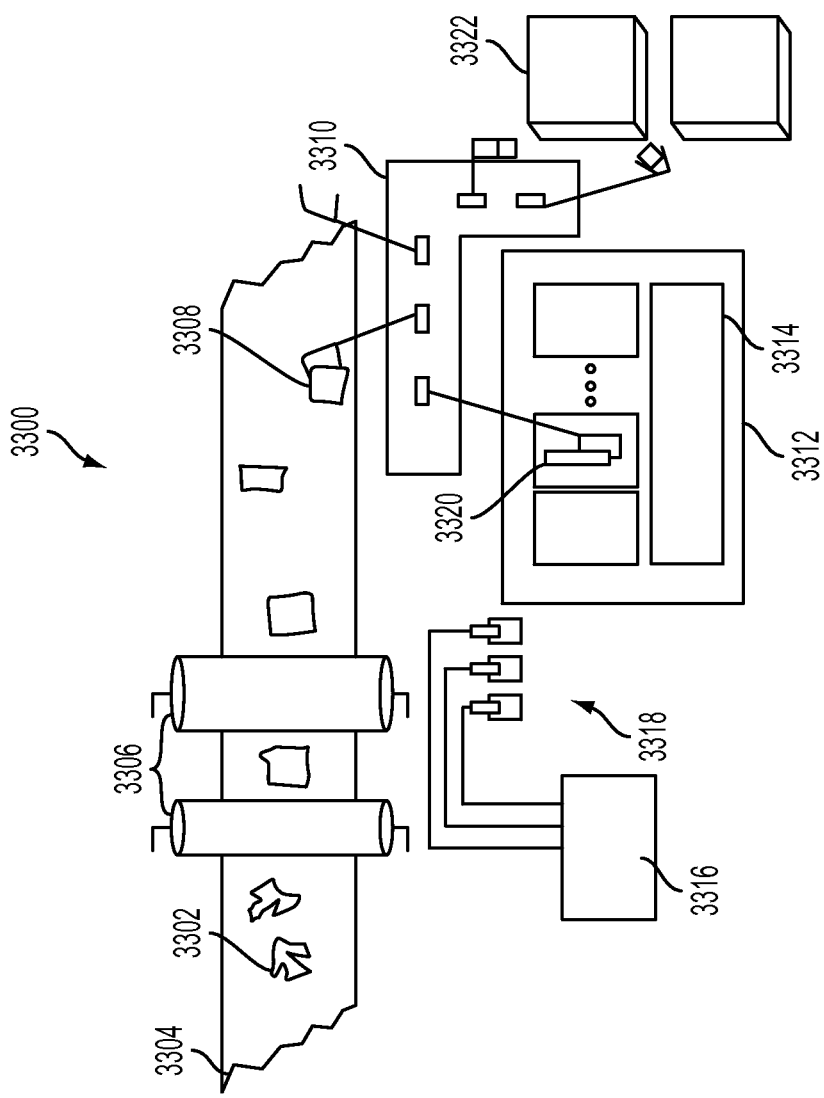
FIG. 33 illustrates an alternative implementation of a bulk system of sorting according to the present application.
Figure 34:
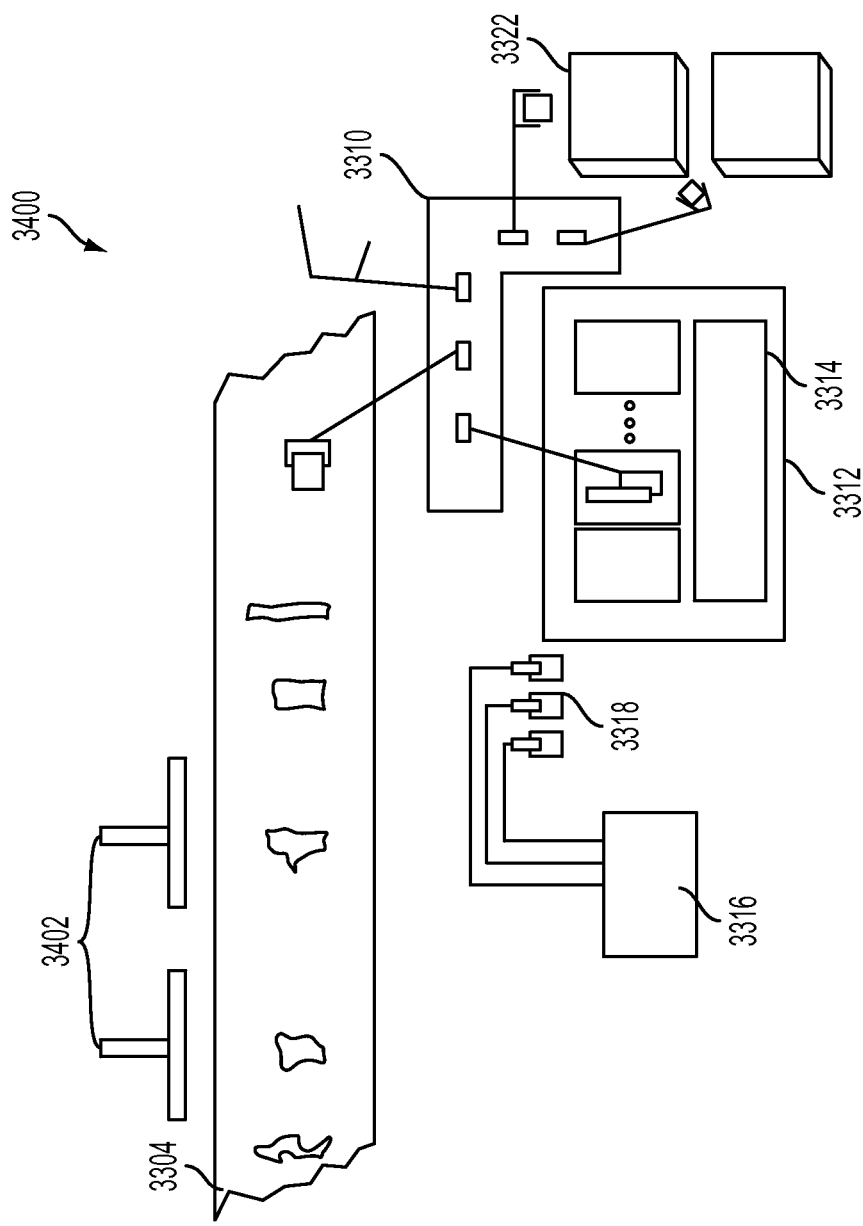
FIG. 34 depicts a bulk separation testing system according to the present application.

As will be expanded upon in FIGS. 33 and 34, the mentioned bulk sorter environments include a source of metal or alloy scraps, which are separated, and then individually tested and sorted according to the test results.

Figure 15:
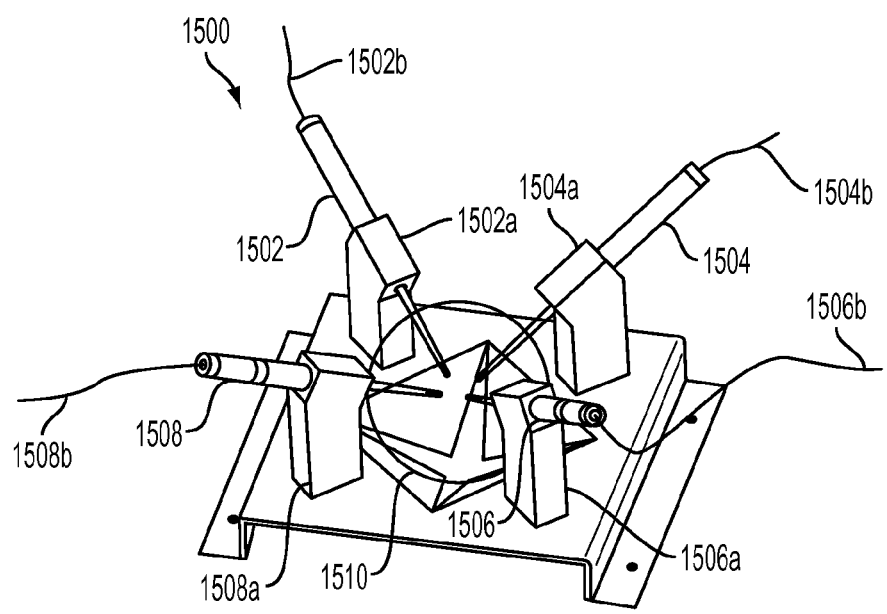
FIG. 15 illustrates a multi-pointed metal probe system for obtaining an electrical connection for testing purposes.

Another connection embodiment is shown by system 1500 of FIG. 15 where pointed metal probes 1502, 1504, 1506, 1508 are pneumatically driven into the scrap 1510 by pneumatic driving mechanisms 1502*a*-1508*a*. Once driven into the metal or alloy (in one embodiment relatively soft aluminum) 1510, the probes form a direct electrical connection with fresh metal or alloy. Then an electrical line or electrical lines 1502*b*-1508*b* are provided from one or all of the probes 1502-1508 to the testing components (e.g., test system 1414 of FIG. 14). In one embodiment all four electrical lines may be tied together and then a single electrical line provided to the test system, or each individual line is provided to the test system. It is to be understood, other mechanical or electromechanical devices could be used to drive such probes to the metal or alloy 1510, as will be apparent to one skilled in the art. For example, for a bulk sorter, a plurality of these probes can also be used for fixturing the scrap as shown in FIG. 15. Particularly, when several of these probes 1502-1508 are thrust towards the sample (e.g., scrap) from different angles, then between them they are used to hold the scrap in place for the later testing steps.

As previously mentioned in this disclosure, techniques that can also be used to remove electrical insulators on the surface of the metal alloy or alloy (e.g., 1408, 1510, etc.) include grinding, milling, sanding, and in addition to these techniques, the removal can also be accomplished by sandblasting, or other arrangements for abrading the surface, before simply touching an electrical contact to the cleaned metal or alloy being tested.

If the surface is prepared for the test probe (as discussed in the next section), then some portion of that prepared surface may also be touched by an electrical contact (creating a common connection). This is a particular embodiment useful for a handheld type testers or sorters.

Surface Preparation for Electrochemical Cell

The surface of the metal or alloy piece (e.g., in some situations scrap metal or alloy) where the electrolyte is to interact must be sufficiently free of electrical insulators for the electrochemistry to work. Such insulators include paint, oil, and anodized finish and the native aluminum-oxide layer that naturally forms on a metal or alloy (e.g., aluminum alloy) when exposed to air. The present systems are not providing just a purely electrical connection, but an electrochemical one, so a certain minimum area of clean contact must be achieved.

The particular technique used for preparing the metal or alloy surface will depend upon: the size, shape, and surface condition of the metal or alloy whether nitrogen, dry ice, significant electrical and/or pneumatic powers are available. These techniques can be broken into four broad categories: chemical, direct mechanical, indirect mechanical, and impact.

In all these cases, there is a limited time-window between cleaning, and the natural re-forming of the native oxide layer. This then requires rapid application (in some cases within seconds) of the electrochemical probe operation to the newly prepared surface, or else the exclusion of oxygen from the region until the electrochemical probe can be applied. In one preferred embodiment, the site is flooded with nitrogen gas until the test is completed.

Chemical

Chemical techniques involve some acid, base, solvent, or other chemical(s) being applied to the surface (e.g. wiped or sprayed) to remove the surface insulators. Once the surface is sufficiently cleaned, it is important that both the cleaning chemical, and byproducts from the cleaning chemical's interaction with the surface insulators, not interfere with the subsequent electrochemical step. This can be achieved through careful selection of the cleaning chemical, or though removal of the chemical (and byproducts) by a second cleaning step. Such removal could be achieved through dry wiping, evaporation, or wiping with still further chemicals. In one embodiment, hydrazoic acid can be used for the cleaning step, followed by a dry wipe. Hydrazoic acid is a strong reducing agent, which decomposes into gaseous products.

Direct Mechanical

A particular approach is to cut, scrape, or abrade the surface until sufficient fresh metal is exposed. In certain embodiments this may be accomplished through a pneumatic- or motor-driven tool applying a: milling bit, sandpaper, or grinding disk to the metal scrap's surface. In the case of grinding or sanding, it is desirable that the material should be chosen such that small amounts of residue will not impact the subsequent electrochemical testing. A mechanical wipe, or jet of air, can be used to remove the residue. The flow of air over the site to be cleaned may enhance the rate at which native oxide reforms. Therefore use of an inert gas such as nitrogen or carbon dioxide mitigates this issue. One particular embodiment is a rotary motor spinning a nylon mesh disk embedded with ceramic alumina, where residue is blown off with nitrogen.

A handheld, battery powered rotary tool can be used in conjunction with a handheld sorter.

Indirect Mechanical

Indirect methods can also be used to prepare the surface of the metal or alloy, for example sand-blasting. Most practical in the bulk sorter, this has an advantage of naturally conforming to non-flat, non-smooth surfaces (such as crumpled metal or alloys). Different materials can be used for the abrasive particles. Preferably the material is chosen such that small amounts of residue will not impact the subsequent electrochemical test. One particular material that may be used is silicon carbide. As the flow of air over the site to be cleaned may enhance the rate at which native oxide reforms an inert gas such as nitrogen or carbon dioxide may be used as the propellant to mitigate this issue. Using small pieces of solid carbon dioxide ("dry ice") as the abrasive results in no (zero) residue (i.e., it will evaporate) while simultaneously reducing the reforming of the native oxide layer.

Impact

Figure 16:
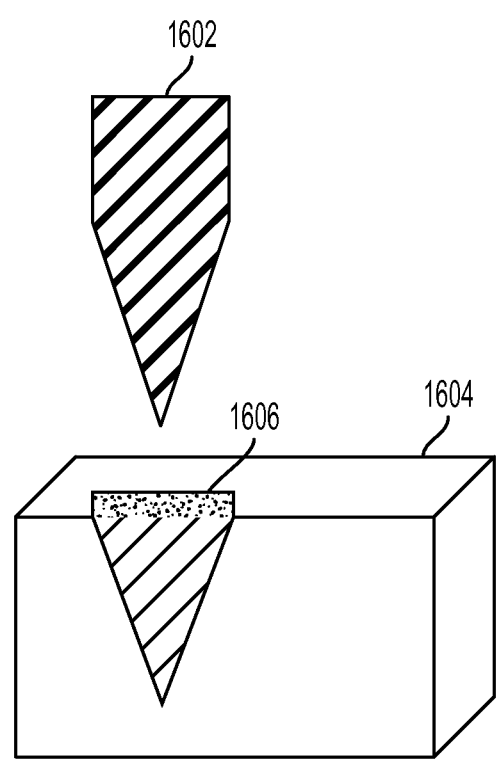
FIG. 16 illustrates an impact probe use impact probe used to obtain a clean section of metal or alloy for testing purposes.
Figure 17:
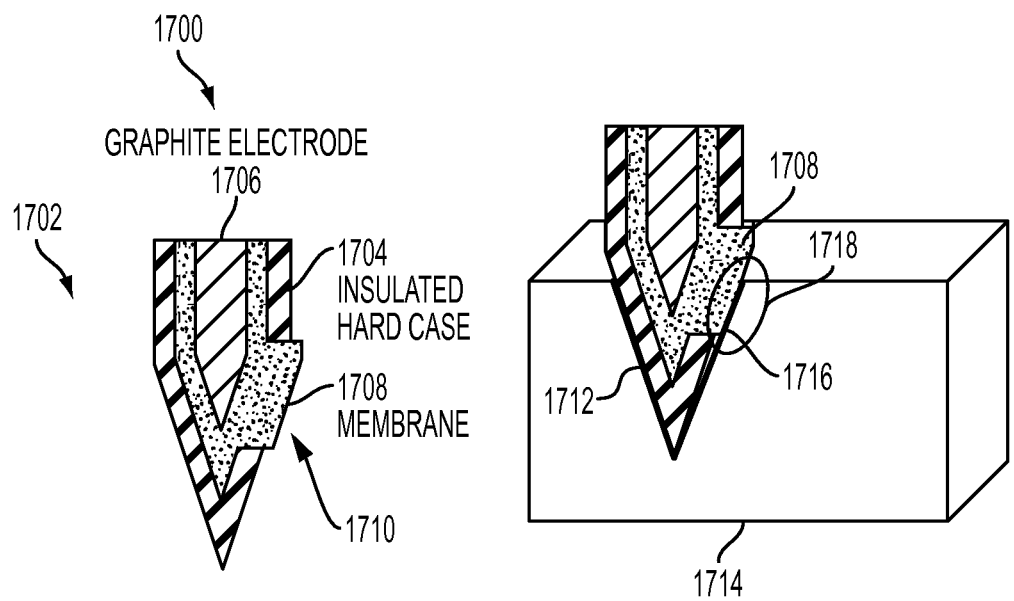
FIG. 17 illustrates the concepts of FIG. 16 shown within a metal or alloy sample.

Turning to arrangements 1600 and 1700 of FIGS. 16 and 17, illustrated are examples of impact type embodiments. One solution is to pneumatically drive a pointed metal probe into the metal or alloy, in a manner similar to that described in the above section "Metal Or Alloy Sample (e.g., Scrap) As An Electrode." As shown in FIG. 16 such a probe 1602 has been driven into sample 1604, and then removed, leaving a crater 1606. Mechanical or electromechanical devices other than pneumatically based devices may also be used to drive probe 1602, as will be apparent to one skilled in the art. In particular embodiments, after probe 1602 is withdrawn from the scrap or sample 1604 (leaving a crater), an electrolyte and test probe or electrode (not shown) are then directly introduced into the crater 1606. Alternatively a membrane carrying the electrolyte could be introduced into the crater 1606 along with a test probe.

In the case of dripped electrolyte, a small non-conductive tube (e.g. a glass pipette) or saturated membrane could convey electrolyte into the probe's crater, while maintaining an unbroken column of liquid back to the electrode. This method consumes more electrolyte per sample, but eases its introduction into a small crater.

Alternately, as depicted in arrangement 1700 of FIG. 17 an impact-test probe 1702 may be constructed in a manner that allows the impact-test probe 1702 to remain in a crater formed in the metal or alloy scrap, with the membrane or electrolyte dispenser integral to it. More particularly impact-test probe 1702 includes an insulated hard outer case 1704, having a sufficient strength to penetrate the sample to be tested. A test probe electrode 1706, such as a graphite electrode, is located within the insulated hard outer case 1704. FIG. 17 further shows a porous membrane section 1708, where at least a portion of the membrane fits within a cutout section 1710 of the hard outer case 1704. The right-hand side of FIG. 17 shows (in a cut-away view) the impact-test probe 1702 embedded in a crater 1712 of a metal or alloy sample 1714. Fresh clean metal or alloy 1716 is exposed by the probe's penetration. The circle 1718 shows the portion of fresh metal or alloy 1716 in contact with the electrolyte-wetted membrane 1708. It is to be understood the hard outer case 1704 needs to be harder than the scrap metal or alloy 1714, but not brittle (to withstand the impacts), impervious to the electrolyte and electrically non-conductive.

Multiple Probes

Figure 18:
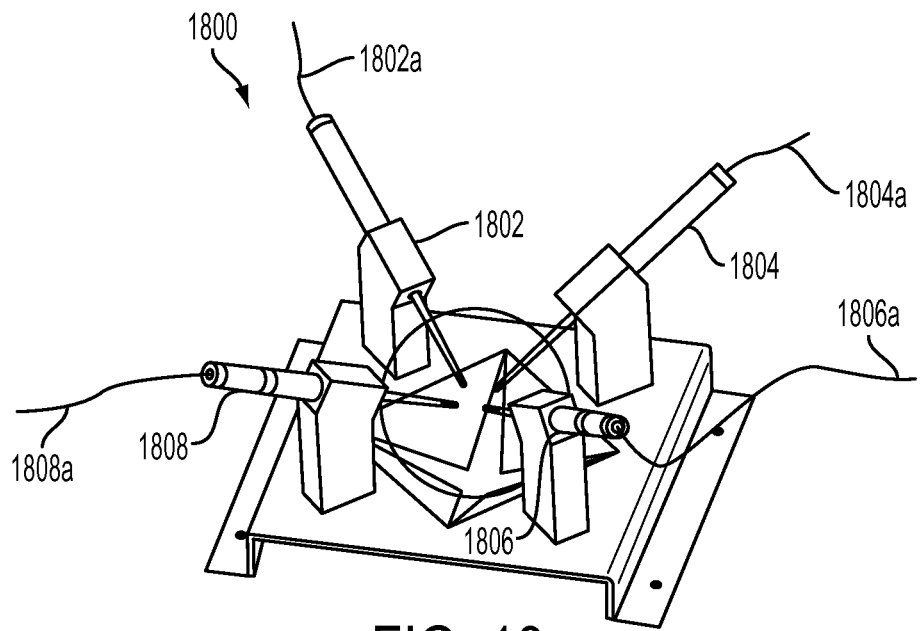
FIG. 18 illustrates a multi-probe system according to the teachings of the present application.

Turning to multi-test probe arrangement 1800 of FIG. 18, the number of test probes 1802, 1804, 1806, 1808 required for a particular use will vary depending upon the desired output (e.g. testing for a family of metal or alloy, or for a specific alloy, or production method) and also what is already known about the metal or alloy sample (e.g. knowing that it is either 5000 or 6000 aluminum alloy families). In some cases, one system or test probe may be sufficient; in other cases several test probes working with different electrolytes may be needed. This section teaches positioning and use of multiple test probes.

In certain embodiments, only one system or test probe 1802, 1804, 1806, 1808 is electrically active at a given time (i.e., electrical connection lines 1802a, 1804a, 1806a, 1808a, which lead back to a testing system such as test system 1414 of FIG. 14) when testing a particular metal or alloy sample; the inactive probes are electrically isolated. With the process taking as little as 100 ms, then this serial approach has little impact on throughput.

In the case of a bulk sorter configuration, these multiple probes can be fairly independent. In fact in the case of the impact test probes an appropriate distance should separate the test probes to avoid interference. If impact-test probes are doubling as a fixturing mechanism, then the locations will be mostly dictated by that role: e.g. four probes coming in towards a single point above a passive holder as shown in FIG. 18.

If direct mechanical methods are employed, then in certain embodiments it may be more efficient to prepare just one surface region, and contact all system test probes and possibly a common probe (e.g., also called sample or scrap probe) electrode at the single location. If the test probes are close enough, then there is some risk of electrolytes from one test probe contacting an adjacent next test probe or the common probe. This situation could "short out" (or bypass) the electrochemical cell, and/or may contaminate the test probe(s) and/or common probe for future tests. If the test probe(s) and/or common probe are to be used in close proximity, then having a chemically resistant compliant seal (e.g. a Viton fluoroelastomer O-ring with a 75A durometer) around the probe(s) reduce this risk.

FIGS. 19, 20 and 21 illustrate three system test probes 1902, 1904, 1906 and one common probe electrode 1908 provided in a single body structure 1910. These have been arranged to all touch a defined compact region on the sample metal or alloy, that can be cleaned, for example with a rotary tool. As shown by view 1900 of FIG. 19, the test probes and common probe electrodes 1902, 1904, 1906, 1908 are recessed into single body structure 1910 and as shown best in view 2100 of FIG. 21 are independently spring loaded via corresponding spring arrangements 1902b, 1904b (not fully shown), 1906b, 1908b.

When this single body probe assembly 1910 is pushed towards a flat, prepared surface of the sample (or scrap), O-rings 1902a, 1904a, 1906a (as partially seen in view 2000 of FIG. 20) first make contact and compress to seal face 1912 against the metal or alloy sample that is to be tested. With further pressure, the three system test probes 1902, 1904, 1906 advance, via the spring arrangements until they each make contact with the sample surface. Further pressure brings the common (scrap) probe electrode 1908 into contact with the metal or alloy sample. The electronics of the test system (e.g., 1414 of FIG. 14) can detect the OCV (Open Circuit Voltage) between the common (scrap) test electrode 1908 and any one of the system test probes (e.g., electrodes) 1902, 1904, 1906.

Since the common (scrap) probe electrode 1908 is the last to make contact (by virtue of being recessed further as can be seen by view 2000 of FIG. 20), then the test system can be sure that all test probe electrodes are in contact with the metal or alloy sample, and the test can commence. Applying a small current between the common probe electrode 1908 and the particular test probe electrode being observed (I.e., one of test probes 1902, 1904, 1906) will create a more easily detected trigger signal. The signals are provided via connection lines 1902c, 1904c (not fully shown), 1906c, with a common connection line 1908c.

These compact, spring-actuated assemblies are useful with the handheld arrangement where holding probes in such a way as to make multiple independent, or widely spaced locations, would be difficult. Having to prepare only a single region on the metal or alloy sample is also helpful in the handheld case.

Figure 22:
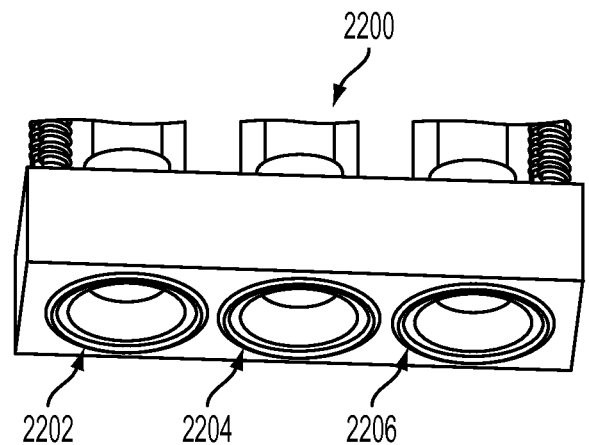
FIG. 22 depicts an alternative embodiment of a multiple test probe arrangement similar to the previous FIGS. 19-21, but wherein the three test probes are aligned with each other.

It will be apparent to one skilled in the art that other configurations in different shapes, or with different numbers of probes, are also possible. For example, FIG. 22 illustrates a linear design 2200 with three system test probe electrode configurations 2202, 2204, 2206; where the common connection is made through a vise jaw with a serrated pattern, or other connection arrangement (not shown in this figure but shown in FIG. 14). It is to be understood the test probes of FIGS. 19-22, may contain the same or different electrolytes as other test probes in such arrangements. The determination depending upon the particular implementation.

Also, in multiple probe devices (for both the bulk test arrangements and handheld arrangements), not all system test probes need be in contact with the surface of the metal or alloy sample at once. For example, in particular bulk sorter arrangements, different test probes containing different electrolytes could be applied at successive stations in the sorting system. In fact the results from one test may be conclusive enough to cause a metal or alloy sample to be diverted before the next test probe is applied (saving wear/use of that next test probe).

Figure 23:
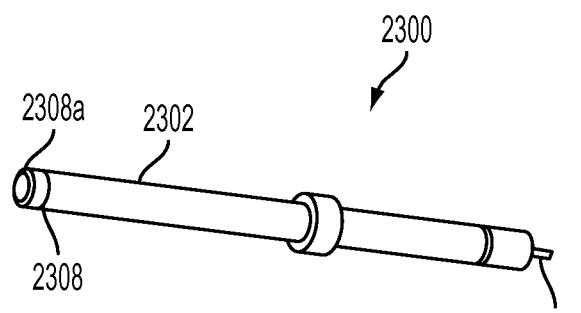
FIG. 23 depicts a view of a test probe cartridge.
Figure 24:
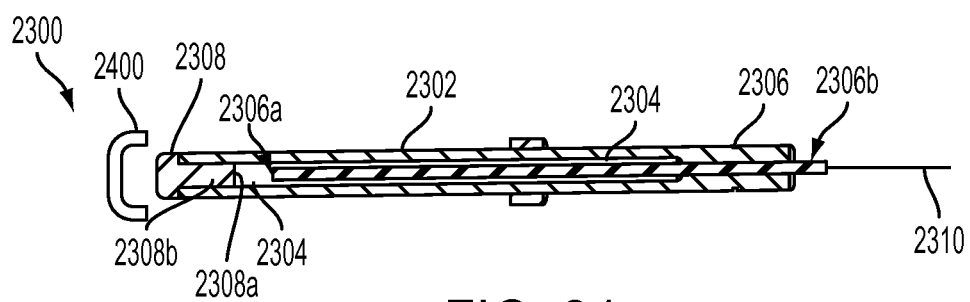
FIG. 24 shows a cross section of FIG. 23.

Turning to FIGS. 23 and 24 illustrated are different views of an electrolyte test cartridge 2300, including an electrolyte tube 2302, holding an electrolyte 2304, a test probe electrode 2306, and electrolyte membrane 2308. In this embodiment, the membrane 2308 is a porous polyethylene; the electrolyte tube 2302 is a high-density polyethylene or peek; and the test electrode 2306 is an electrode glassy carbon. It is however to be appreciated these materials are just given as an example and the components of cartridge 2300 may be configured of other materials. Cutaway view of cartridge 2300 of FIG. 24, shows that electrolyte 2304 is between an end 2306a of test probe 2306 and an end 2308a of membrane 2308, as well as surrounding other parts of the test probe electrode 2306. It is further shown that membrane 2308 is formed in a t-type configuration with an elongated section 2308b entering into the interior of tube 2302. Additionally, a second end 2306b of the test probe electrode 2306 is designed to have an electrical connection line 2310 which is connected back to the test system components as previously discussed.

The disclosed test probe 2300 is relatively simple, and in some embodiments may be considered to be disposable (i.e., the electrolyte fluid would not be replaced; rather a new cartridge would be inserted to replace the spent cartridge). One potential issue with cartridge 2300, would be the drying out of the electrolyte (especially on the surface of the test probe), undesirably concentrating the electrolyte. A cap 2400 configured to fit over membrane of the test probe electrodes in a substantially air tight manner may be used to mitigate this issue.

In an alternative embodiment (see FIGS. 25-30), the cartridge 2300 of FIGS. 23 and 24 may be designed as cartridge 2500 designed to contain a valve arrangement 2502 near the membrane end of the cartridge 2500. Other than the valve arrangement 2502 cartridge 2500 is designed in a manner similar to that as described in connection with cartridge 2300 of FIGS. 23 and 24.

FIGS. 25 and 26 depict valve arrangement 2502 in more detail, to show that valve arrangement 2502 is configured to dispense electrolyte (in certain embodiments in a fixed volume) when the valve arrangement is in an open position. For example in this embodiment, a wave washer or compressed foam ring 2600 of FIG. 26 is positioned around the narrower section of the t-shaped membrane 2506, between one end of tube 2504 and a surface of the wider portion of membrane 2506. In this position the wave washer or compressed foam ring 2600 acts to push an end portion 2508 of the t-shaped membrane 2506 out or away from tube 2504. By this action an upper u-shaped portion 2510 of membrane 2506 grabs and pulls a stem 2512 of flexible closing element (a mushroom shaped component) 2514 against a rigid valve base 2516. This position seals the t-shaped membrane 2506 from electrolyte within the body of tube 2504. More particularly, as shown in view 2700 of FIG. 27 and view 2800 of FIG. 28, closing element 2514 and valve base 2516, when in contact with each other are designed to block fluid flow. This is shown when reviewing exploded view 2800 of FIG. 28 which more clearly shows that closing element 2514 includes openings 2514a, 2514b, 2514c, 2514d. FIG. 29 more clearly shows that the valve base 2516 includes an opening area 2516a. In the closed position (as seen in view 3000 of FIG. 30), these openings are offset from each other to stop fluid flow to the membrane 2506. Particularly, when surface 2516b of valve base 2516 is located against surface 2514e of closing element 2514, no fluid (e.g., electrolyte) will flow to membrane 2506. However, when the tip 2508 of the membrane 2506 is pressed against a surface of a metal or alloy sample, the closing element 2514 flexes inwards and the valve is opened allowing fresh electrolyte to flow from the interior of tube 2504 through openings 2514a-2514d and 2516a to the membrane 2506.

These single cartridges are easily field-replaceable (especially useful in the handheld case). Different tubes could be color-coded, or marked with symbols or lettering to guide the user to insert the correct cartridge into the correct slot. The user may choose not to fill all slots for certain applications, and may be guided by the user interface (see later section) as to which cartridges are important for a particular implementation.

In certain embodiments, the cartridge (2300, 2500) contains communication components to electronically communicate to the test system some or all of: electrolyte type, capacity, factory-fill date, and per-probe calibration data. This could be done though a factory trimmed/tuned resistor or capacitor, through use of an EEPROM, or other communication equipment. If a reprogrammable memory is fitted to each probe, then such values as: number of measurements made, first use date/time, most recent use date/time could all be recorded. This further information would let the system calculate (and display to the user) the useful life remaining in the test probe, or allow drift calculations to be performed. One skilled in the art will see other ways of communicating/storing this information, and other items that could be communicated or stored.

Handheld Sorter

In one preferred embodiment, handheld sorter 3100 of FIGS. 31 and 32 is designed with a flat surface 3102 on which it can rest, with an integral handle 3104 for easy holding in a single hand. It may also incorporate a surface preparation device (e.g., a rotary chuck which can hold and spin a circular abrasive disk) 3106. It may also contain a small cartridge of compressed fluid (e.g., CO2 or N2) 3108. The output of this cartridge being valved by a user, and directed through an output tube 3110 so as to blow the prepared surface clean of residue after the surface has been abraded. The use of a non-oxygen bearing gas reduces the reformation of the native oxide.

A probe cartridge holder 3112, such as discussed in connection with FIGS. 19-24, for holding multiple test probes and a common probe (such as discussed in connection with FIGS. 14-17 and 19-21), is also incorporated into the handheld device 3100, where the test probes of cartridge holder 3112 are connected to an onboard test system as previously disclosed.

The handheld sorter 3100 can be powered from a primary or rechargeable battery 3114, or optionally an external electrical source (e.g. an AC power supply, not shown). The batteries could be standard size (e.g. AA), fixed integral, or modular units similar to that of a power drill.

User Interface

In the handheld tester embodiments, a user interface 3200 shown in FIG. 32 is provided in the form of a input/output screen. It is to be understood that the user interface 3200 can also be designed in other configurations including voice activated systems, LEDs, etc. The more the user knows (and informs the handheld device through the user interface) about what the sample metal or alloy could be, then the better results it can give, e.g. a test that gives ambiguous results between 5xxx and 7xxx series aluminum alloy can be easily resolved in the correct direction if the device is informed that the sample is either 5xxx or 6xxx. While the foregoing has mentioned that the sample metal or alloy may be scrap metal, the present concepts could also be employed with newly formed metal or alloy that is configured in a roll configuration, flat plane configuration, among others.

Unless (as described earlier) the cartridge contains a method of automatically communicating to the test system, then a user may be required to enter information about a test probe cartridge each time it is changed (including electrolyte type, capacity, factory-fill date, and per-probe calibration data). The sockets for each cartridge may be keyed or color/symbol coded to ensure the correct probe is in the correct spot. However in some embodiments, there are more probe types than slots, and the user must indicate what type of probe has been inserted.

Knowing the desired tests and current probe configuration, the system can advise the user to add/remove/change cartridges. Knowing one or more of the cartridges capacity, manufacture date, initial use date, and number of tests, the system can advise the user to replace an older cartridge.

Of course key information to the user is the test system's output, one or more of: family (e.g. the 6000 series alloys of aluminum), or a specific alloy (e.g. type 6061 alloy), or by chief alloying agent (e.g. >1% Copper), or production method (cast vs wrought). With possible uncertainty in the result, the system can provide confidence indicators, or even list multiple candidates with respective probabilities. These answers can be audible or visual (e.g. an LCD display showing text). In the case where the user has configured a simple test ("check that everything is 5xxx" or "sort between 5xxx and 6xxx") then a small number of indicator lights may suffice, and be faster to act upon (e.g. green="yes, it is 5xxx", red="something else detected").

In other embodiments a more tactile is used by vibrating the handle when a test is complete, or (conversely) to indicate that it should be repeated, or that an anomaly has been detected.

The system can provide feedback to the user on whether a test was successful (high enough confidence), or if the system recommends repeating the surface prep and test. This too can be audible or visual.

User input can be some combination of buttons, switches, and voice commands. In one preferred embodiment, the user input (and output) can be via another piece of equipment (e.g. a phone or tablet) in wired (e.g. USB) or wireless (e.g. Bluetooth) communication with the handheld. Such communication with a separate piece of equipment is particularly useful in setting up a series of tests, and reporting aggregate results at the end of a session or shift.

Bulk Sorter

The handheld sorter and bulk sorter arrangements are particular points along a spectrum for implementation of the ionic testing concepts. The following sections discuss further arrangements that may be employed in such embodiments where, while not limited to the bulk sorter arrangements, do have useful applications thereto.

Singulating and Fixturing

The input stream of scrap may come directly from a pile or from the back of a truck, or manually shoveled into the system. In certain embodiments, these all result in a disorganized pile of scrap on a conveyor belt. In the testing system 3300 and 3400 of FIGS. 33 and 34 respectively, the testing systems teach that each piece be individually held (or fixtured) while under test. Various methods of singulating the disorganized pile are known to those skilled in the art, but include pick-and-place claws and shaker tables.

Once singulated, the piece of scrap must be held with respect to first the surface preparer, and then with respect the test probe(s). Many options exist (e.g. vises, claws, and clamps), however scrap metal can have a wide range of unpredictable, and complex shapes. One preferred embodiment is the plurality of pointed metal probes driven pneumatically into the scrap as described earlier. These adapt well to the unpredictable shape of the scrap, and also server as the scrap electrode.

An alternative to adapting the fixturing to the unpredictable shape of the scrap, is to change the shape of the scrap to a more uniform or convenient shape to fixture. For example, and as detailed more fully in connection with FIGS. 33 and 34, a pair of rollers could cold-roll any input scrap into a poor-quality plate of known thickness. In another embodiment, the system could be configured with several plates that are actuated so as to press the incoming scrap into a rectangular prism. In either of these cases, the fixturing system is simplified and made more reliable.

For increased throughput, testing process can be broken into two or more sequential stations, and the fixturing device may move (carrying the scrap) through several steps of the testing; e.g. surface prep, test with first probe, test with second probe, then release.

Probe Placement

Choosing which part(s) of the surface of the unpredictable shaped scrap to prepare and to place probes on can be a challenge to do automatically. Ideally the placement is chosen so as to maximize the probe-tip to scrap contact area: so perpendicular, and in the middle of a flat region (not resting on a "peak" or half-off a step). This may require either the probe and/or the scrap holding device to move in several axes. A vision system can be used to direct placement. Obviously, the surface preparation must be applied to (at least) the same areas as the probe will be placed. Given the difficulty of reliably choosing and preparing the regions, then in one embodiment, multiple probes of the same type are placed at different places on the same piece of scrap. The highest-confidence result, average result, confidence-weighted average result, or some other combination of the electrochemical responses from these probes can be used for the final determination.

If the rolling or compressing techniques described in the previous section are employed, then probe placement and surface preparation is simplified. For example, if cold-rolled into a flat horizontal sheet, a vertically mounted test probe will always be directed perpendicularly at a large expanse of flat surface.

Calibration Sample

Particularly useful in the bulk sorter, where the number of tests performed is large, periodic placement of the probe(s) against a one or more known test samples can help with calibration. By occasionally applying the test system to the known samples, the current accuracy of the system can be evaluated.

This can be used to: trigger probe cleaning, trigger membrane replacement, or to update a table of calibration values used to correct electrode "drift".

Output

In the automated/bulk sorter, one use is to sort the incoming stream of metal or ally into a plurality of output streams. This sorting could be by family, alloy, etc., or by exception, e.g. everything that is not 5xxx goes into the reject stream. To do this, a diverter after the testing operation has been completed is controlled by the test system. This diverter can be one or more of: a diverting paddle, a pusher, a trap-door, or one of many other methods known to those skilled in the art, a particular showing of a diverter arrangement is shown by the conveyor system of FIG. 10.

Depending upon the particular application, for metal or alloys pieces the test system has low-confidence in its identification can be either treated as the closest match found, or sorted into a reject stream. Depending upon the economics, this reject stream could be optionally re-routed to the input stream for re-testing. The down side of this is that some very poor scrap (e.g. a rock) will repeatedly be circulated. As an alternative, a low-confidence test can be kept fixtured and the test repeated a number of times. In this case, after a set number of poor readings, the scrap can be considered impossible to test, and sorted on that basis.

In another embodiment, the system does not sort, but passes all pieces on. Its job then is to periodically provide cumulative assays of the scrap stream. This is a cheaper option than a full sorter, but allows the secondary smelter to at least know what is about to enter their furnace, and prepare additions appropriately.

Bulk Sort Implementations

While a variety of implementations of bulk sorting systems may be implemented using the foregoing descriptions, FIGS. 33 and 34 provide two specific implementations.

Turning to FIG. 33, system 3300 includes having scrap metal 3302 moved along a conveyor system 3304. As scrap metal is often crumpled or otherwise deformed, a particular implementation may use a cold rolling system 3306 (in this case using two cold rollers), whereby as the scrap metal moves on conveyor belt 3304, it is successively moved into a flattened or more linear piece of metal or alloy. As a compressed piece of metal or alloy, for example, 3308 reaches a predetermined position, a pick-and-grab system 3310 may be used to move a piece of the flattened metal or alloy to a holding station 3312, such as previously discussed. This may include pneumatic holding or other known types. Holding station 3312 may also incorporate a cleaning station 3314, which will clean the metals in a manner as previously discussed. Once cleaned and fixed, the test system 3316 will provide test probe or electrode arrangements 3318 in any of the test probe arrangements previously discussed, as well as others which may be obvious to one of ordinary skill in the art and will be moved into position to test a piece of metal or alloy, e.g., 3320. Once testing has been accomplished, a piece of metal or alloy that has been tested may be picked up by another portion of the pick-and-place system 3310 and provided to a sorting area 3322, which may be a variety of locations where similar metals or alloys are positioned for further processing.

Turning to FIG. 34, a similar configuration is shown in bulk sorting system 3400. In this system, many of the components are similar to that previously discussed and therefore will not be repeated. A particular distinction, however, is that instead of roller arrangement 3306, a cold metal stamping configuration 3402 may be used in order to attempt to flatten the metal pieces. With multiple stamps moving in different axes, the metal piece could be shaped into a rectangular prism which presents a flat surface and maintains greater thickness.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A handheld electrochemical metal and/or alloy test system, comprising:
   a cleaning arrangement configured to interact with a surface of the metal and/or alloy to be cleaned;
   an electrochemical test system including an electrically conductive system electrode positioned and configured to form an operable connection between the system electrode and a portion of the surface of the metal and/or alloy to be tested, at least one electrically conductive test probe electrode configured and positioned to form an operable connection between the at least one test probe electrode and a portion of the surface of the metal and/or alloy, an electrically non-conductive membrane, electrolyte, and a signal generating component in electrical connection with the system electrode and the at least one test probe electrode, wherein the at least one electrically conductive test probe is a plurality of electrically conductive test probes and the plurality of electrically conductive test probes and the electrically conductive system electrode are incorporated in a single body structure;
   a user interface configured to input data to the electrochemical test system and to receive data from the electrochemical test system;
   an onboard computing system for interacting with at least one of the cleaning component, electrochemical test system and the user interface;
   a power supply for providing power to the cleaning arrangement, the electrochemical test system, the user interface, and the onboard computing system; and
   a handle area for holding the handheld electrochemical metal and/or alloy test system.

2. The handheld test system of claim 1 wherein the power supply is a rechargeable battery integrated into the handheld system.

3. The handheld test system of claim 1 wherein the user interface includes an electronic display screen.

4. The handheld test system of claim 1 wherein the electrolyte, the electrically conductive test probe electrode and membrane are formed as a test probe cartridge including a tube having an interior in which is carried the electrolyte, a portion of the test probe electrode, and a portion of the membrane, the tube having first and second openings, the first opening sized to allow passage of the test probe electrode into the interior of the tube resulting in a fluidic sealing of the first opening, the second opening of the tube sized to permit insertion of at least a portion of the membrane providing a selective fluidic path for the electrolyte through the membrane.

5. The handheld test system of claim 4 wherein the test probe cartridge further includes a valve arrangement, to allow measured amounts of the electrolyte to move from the interior of the tube into and through the membrane.

6. The handheld test system of claim 4 wherein the test probe cartridge includes onboard communication components to communicate informational data related to the test probe cartridge.

7. The handheld test system of claim 6 further including computing and communication components to receive the informational data from the test probe cartridge, and to provide the informational data to a user.

8. The handheld test system of claim 6 further including computing and communication components to input informational data to the test probe cartridge and to receive informational data from the test probe cartridge.

9. The handheld test system of claim 1 wherein the signal generating component is configured to generate asymmetric excitations.

10. A handheld electrochemical metal and/or alloy test system, comprising:
   a cleaning arrangement configured to interact with a surface of the metal and/or alloy to be cleaned;
   an electrochemical test system including an electrically conductive system electrode positioned and configured to form an operable connection between the system electrode and a portion of the surface of the metal and/or alloy to be tested, at least one electrically conductive test probe electrode configured and positioned to form an operable connection between the at least one test probe electrode and a portion of the surface of the metal and/or alloy, an electrically non-conductive membrane, electrolyte, and a signal generating component in electrical connection with the system electrode and the at least one test probe electrode;
   a user interface configured to input data to the electrochemical test system and to receive data from the electrochemical test system;
   an onboard computing system for interacting with at least one of the cleaning component, electrochemical test system and the user interface;
   a power supply for providing power to the cleaning arrangement, the electrochemical test system, the user interface, and the onboard computing system; and
   a handle area for holding the handheld electrochemical metal and/or alloy test system;
   wherein the cleaning arrangement includes a rotary chuck to hold and spin an abrasive disk which is incorporated in a single body structure, further including the electrochemical test system, the user interface, the on-board computing system, the power supply, and the handle area.

11. The handheld test system of claim 10 further including a holder of compressed fluid being at least one of CO2 and N2 and a nozzle to pass the compressed fluid to the surface of the metal and/or alloy.

12. A handheld electrochemical metal and/or alloy test system, comprising:
   a cleaning arrangement configured to interact with a surface of the metal and/or alloy to be cleaned;
   an electrochemical test system including an electrically conductive system electrode positioned and configured to form an operable connection between the system electrode and a portion of the surface of the metal and/or alloy to be tested, at least one electrically conductive test probe electrode configured and positioned to form an operable connection between the at least one test probe electrode and a portion of the surface of the metal and/or alloy, an electrically non-conductive membrane, electrolyte, and a signal generating component in electrical connection with the system electrode and the at least one test probe electrode,
   wherein the electrolyte, one of the at least one electrically conductive test probe electrode and membrane are formed as a test probe cartridge including a tube having an interior in which is carried the electrolyte, a portion of the test probe electrode, and a portion of the membrane, the tube having first and second openings, the first opening sized to allow passage of the test probe electrode into the interior of the tube resulting in a fluidic sealing of the first opening, the second opening of the tube sized to permit insertion of at least a portion of the membrane providing a selective fluidic path for the electrolyte through the membrane;
   a user interface configured to input data to the electrochemical test system and to receive data from the electrochemical test system;
   an onboard computing system for interacting with at least one of the cleaning component, electrochemical test system and the user interface;
   a power supply for providing power to the cleaning arrangement, the electrochemical test system, the user interface, and the onboard computing system;
   a handle area for holding the handheld electrochemical metal and/or alloy test system; and
   further including a plurality of test probe cartridges and the system electrode incorporated in a single body structure.

13. The handheld test system of claim 12 wherein the plurality of test probe cartridges and the system electrode incorporated in the single body structure are spring loaded for movement to operably engage with the metal and/or alloy being tested.

14. The handheld test system of claim 12 wherein the single body structure includes a flat bottom face with openings to allow passage of the test probe cartridges and the system electrode, and sealing gaskets to allow a sealing contact to a surface of the metal and/or alloy.

15. A handheld method of performing electrochemical testing of metal and/or alloy, comprising:
   cleaning, by a cleaning arrangement configured to interact with a surface of the metal and/or alloy to be cleaned;
   performing electrochemical testing, by an electrochemical test system including an electrically conductive system electrode positioned and configured to form an operable connection between the system electrode and a portion of the surface of the metal and/or alloy to be tested, at least one electrically conductive test probe electrode configured and positioned to form an operable connection between the at least one test probe electrode and a portion of the surface of the metal and/or alloy, an electrically non-conductive membrane, electrolyte, and a signal generating component in electrical connection with the system electrode and the at least one test probe electrode,
   wherein the electrolyte, one of the at least one electrically conductive test probe electrode and the membrane are formed as a test probe cartridge including a tube having an interior in which is carried the electrolyte, a portion of the test probe electrode, and a portion of the membrane, the tube having first and second openings, the first opening sized to allow passage of the test probe electrode into the interior of the tube resulting in a fluidic sealing of the first opening, the second opening of the tube sized to permit insertion of at least a portion of the membrane providing a selective fluidic path for the electrolyte through the membrane;

inputting data, by a user interface, to the electrochemical test system;

receiving data to the user interface from the electrochemical test system;

interacting, by an onboard computing system with at least one of the cleaning component, the electrochemical test system and the user interface;

powering, by a power supply the cleaning arrangement, the electrochemical test system, the user interface, and the onboard computing system; and holding, by a handle area, the handheld electrochemical metal and/or alloy test system; and further including incorporating a plurality of test probe cartridges and the system electrode in a single body structure.

16. The handheld test method of claim 15 wherein the test probe cartridge further includes a valve arrangement, to allow measured amounts of the electrolyte to move from the interior of the tube into and through the membrane.

17. The handheld test method of claim 15 wherein the test probe cartridge includes onboard communication components to communicate informational data related to the test probe cartridge.

18. The handheld test method of claim 15 wherein the signal generating component generates asymmetric excitations.

* * * * *